(12) United States Patent
Nishida et al.

(10) Patent No.: US 11,947,703 B2
(45) Date of Patent: Apr. 2, 2024

(54) DISPLAY DEVICE, INFORMATION TERMINAL, PERSONAL INFORMATION PROTECTION METHOD, PROGRAM, AND RECORDING MEDIUM WHEREON PROGRAM IS RECORDED

(71) Applicant: Hitachi High-Tech Corporation, Tokyo (JP)

(72) Inventors: Masaharu Nishida, Tokyo (JP); Hitoshi Ohtake, Tokyo (JP); Isao Yamazaki, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 583 days.

(21) Appl. No.: 17/267,068

(22) PCT Filed: Aug. 28, 2019

(86) PCT No.: PCT/JP2019/033610
§ 371 (c)(1),
(2) Date: Feb. 9, 2021

(87) PCT Pub. No.: WO2020/050109
PCT Pub. Date: Mar. 12, 2020

(65) Prior Publication Data
US 2021/0312079 A1    Oct. 7, 2021

(30) Foreign Application Priority Data

Sep. 3, 2018  (JP) .................................. 2018-164768

(51) Int. Cl.
*G06F 7/04*       (2006.01)
*G06F 21/62*      (2013.01)
(Continued)

(52) U.S. Cl.
CPC .......... *G06F 21/6245* (2013.01); *G06F 21/84* (2013.01); *G16H 10/60* (2018.01)

(58) Field of Classification Search
CPC ...... G06F 21/6245; G06F 21/84; G16H 10/60
(Continued)

(56) References Cited

U.S. PATENT DOCUMENTS

2006/0239394 A1   10/2006  Fujieda
2008/0013727 A1*   1/2008  Uemura ................ H04N 1/448
                                                       380/243
(Continued)

FOREIGN PATENT DOCUMENTS

CN    107623814 A    1/2018
JP    2006-320714 A  11/2006
(Continued)

OTHER PUBLICATIONS

International Report on Patentability (PCT/IB/338) issued in PCT Application No. PCT/JP2019/033610 dated Mar. 4, 2021, including English translation of document C3 (Japanese-language International Report on Patentability (PCT/IPEA/409), filed Feb. 9, 2021 (nine (9) pages).

(Continued)

*Primary Examiner* — Jeffrey C Pwu
*Assistant Examiner* — Samuel Ambaye
(74) *Attorney, Agent, or Firm* — Crowell & Moring LLP

(57) ABSTRACT

Provided are a program and personal information protection method which are executed by a system which is operated by a medical practitioner, said program and method comprising: a display process of causing a monitor part 2 to display an examination result screen 3 including personal information which identifies a subject; an identification process of identifying the personal information in the examination result screen 3 which is displayed in the display process; and (Continued)

an invalidation process of invalidating the personal information identified in the identification process in a captured image which includes the examination result screen 3. Instances of personal information being displayed in error to outside users are thus reduced in comparison to the prior art, and sharing of examination result information is implemented smoothly.

26 Claims, 21 Drawing Sheets

(51) Int. Cl.
    *G06F 21/84*     (2013.01)
    *G16H 10/60*     (2018.01)
    *H04N 7/16*     (2011.01)

(58) Field of Classification Search
    USPC .......................................................... 726/26
    See application file for complete search history.

(56) References Cited

U.S. PATENT DOCUMENTS

| | | |
|---|---|---|
| 2010/0031014 A1 | 2/2010 | Senda |
| 2010/0124363 A1 | 5/2010 | Ek et al. |
| 2011/0035237 A1 | 2/2011 | Ariyoshi et al. |
| 2014/0280376 A1* | 9/2014 | Kuo .................... G06Q 10/10 707/803 |
| 2015/0332439 A1 | 11/2015 | Zhang et al. |
| 2017/0180605 A1 | 6/2017 | Lim |

FOREIGN PATENT DOCUMENTS

| | | |
|---|---|---|
| JP | 2011-33536 A | 2/2011 |
| JP | 2015-226298 A | 12/2015 |
| JP | 2015-228049 A | 12/2015 |
| JP | 2016-532351 A | 10/2016 |
| JP | 2018-36836 A | 3/2018 |

OTHER PUBLICATIONS

International Search Report (PCT/ISA/210) issued in PCT Application No. PCT/JP2019/033610 dated Oct. 1, 2019 with English translation (four (4) pages).
Japanese-language Written Opinion (PCT/ISA/237) issued in PCT Application No. PCT/JP2019/033610 dated Oct. 1, 2019 (five (5) pages).
Japanese-language International Report on Patentability (PCT/IPEA/409) issued in PCT Application No. PCT/JP2019/033610 dated May 26, 2020, with Annexes (14 pages).
Extended European Search Report issued in European Application No. 19858497.1 dated May 3, 2022 (11 pages).

\* cited by examiner

[FIG. 1]
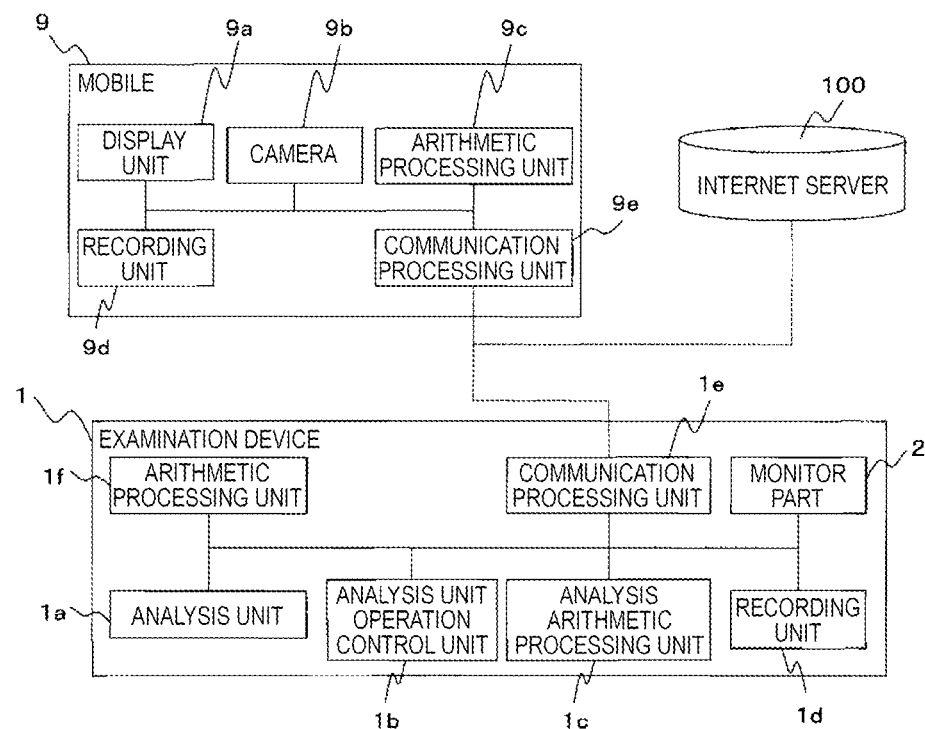

[FIG. 2]
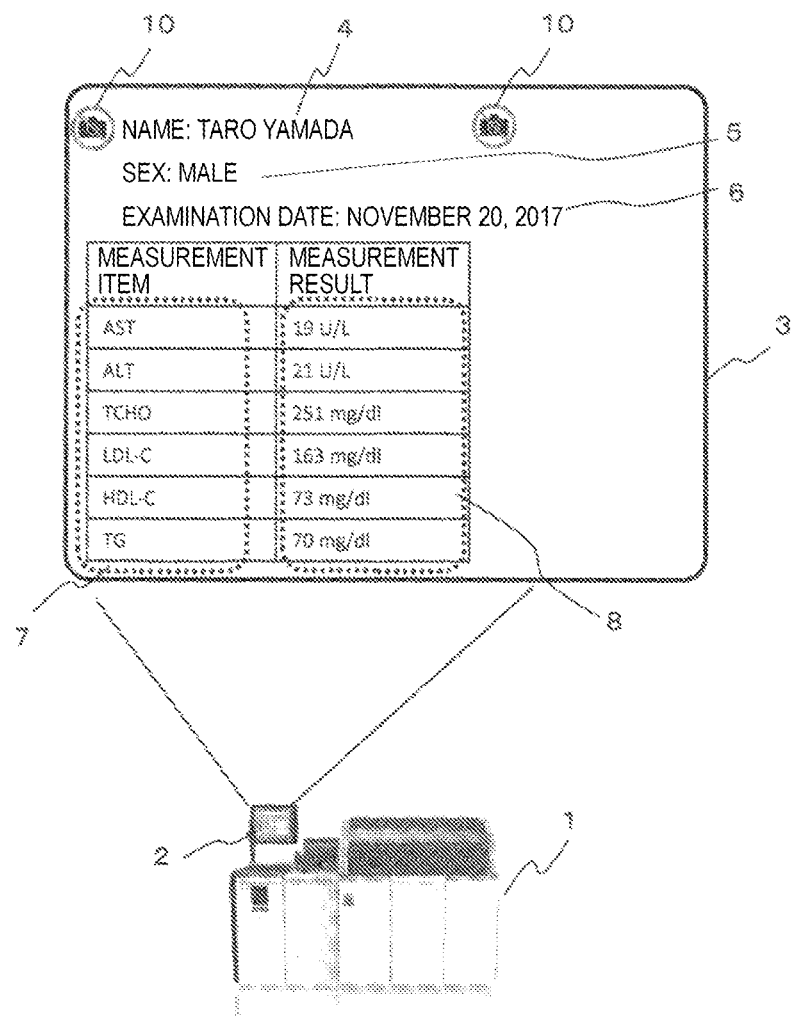

[FIG. 3]
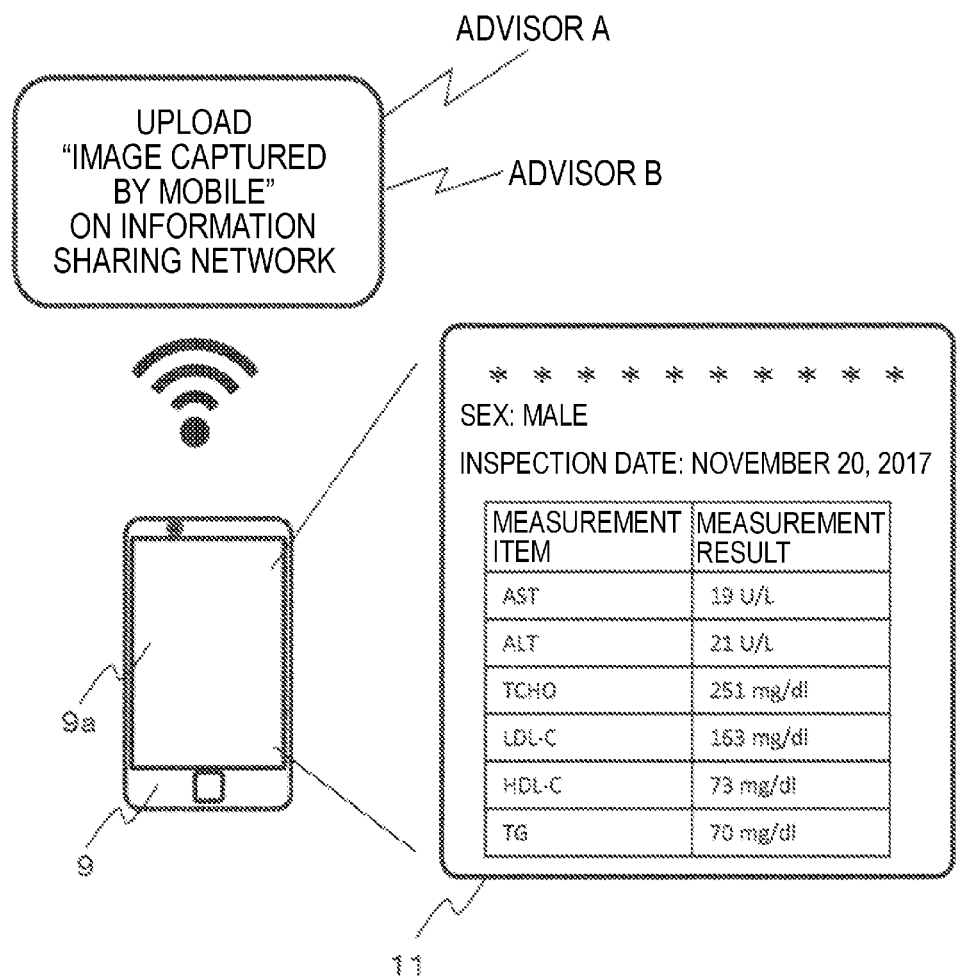

[FIG. 4]
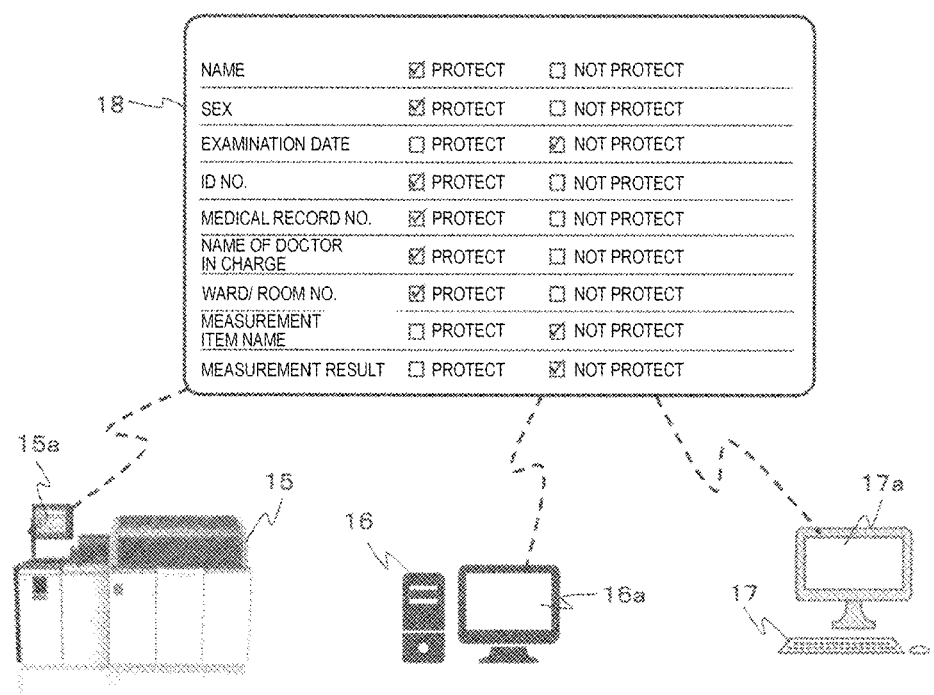

[FIG. 5]
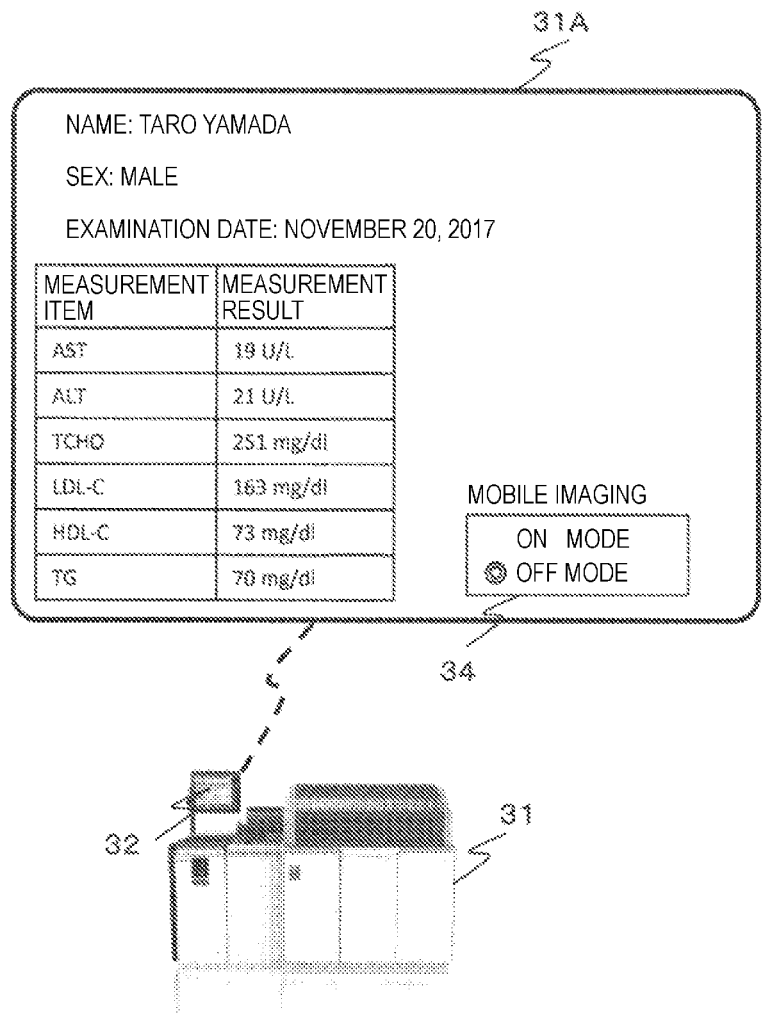

[FIG. 6]
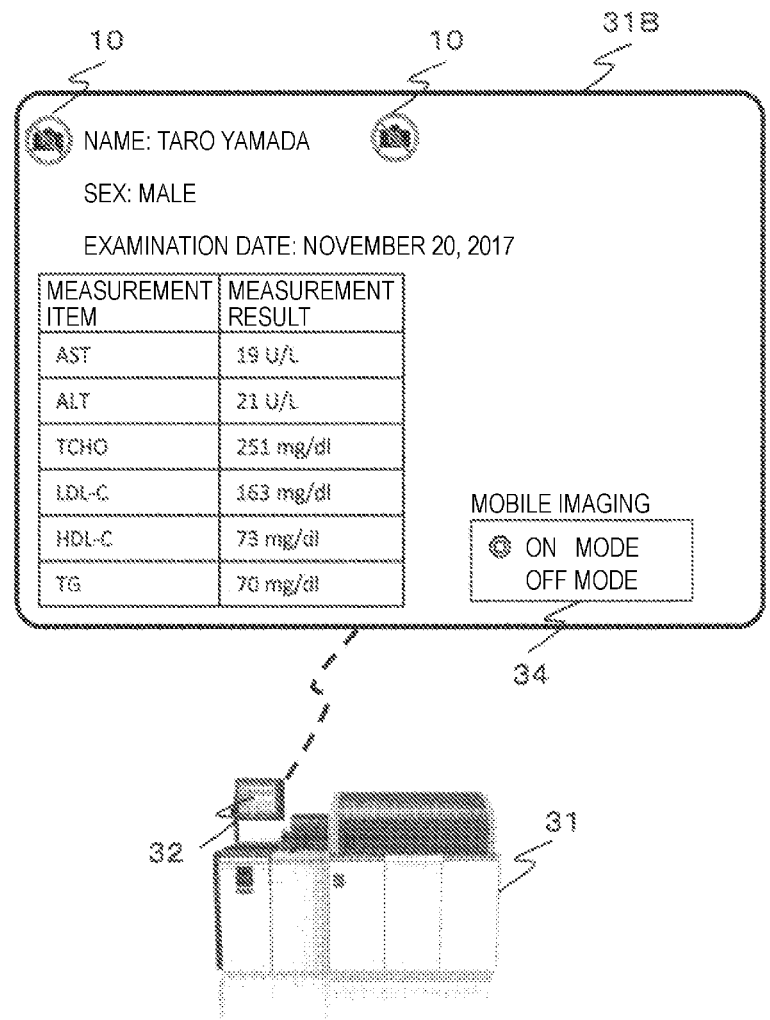

[FIG. 7]
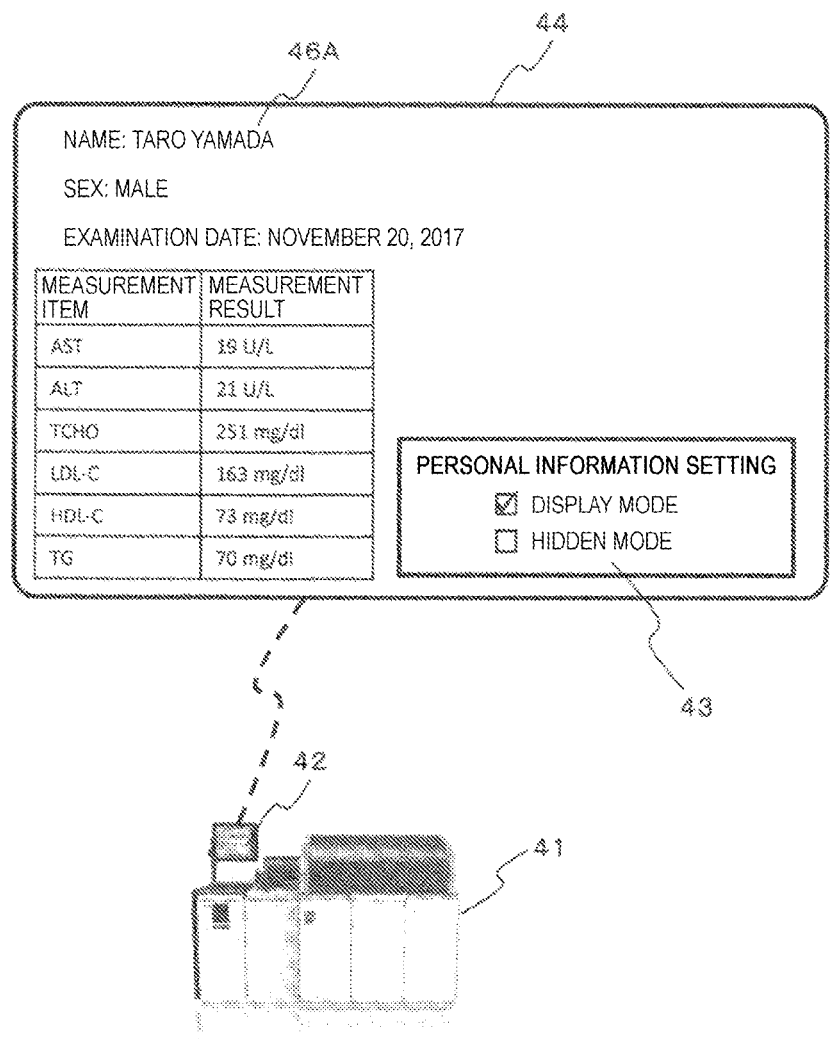

[FIG. 8]
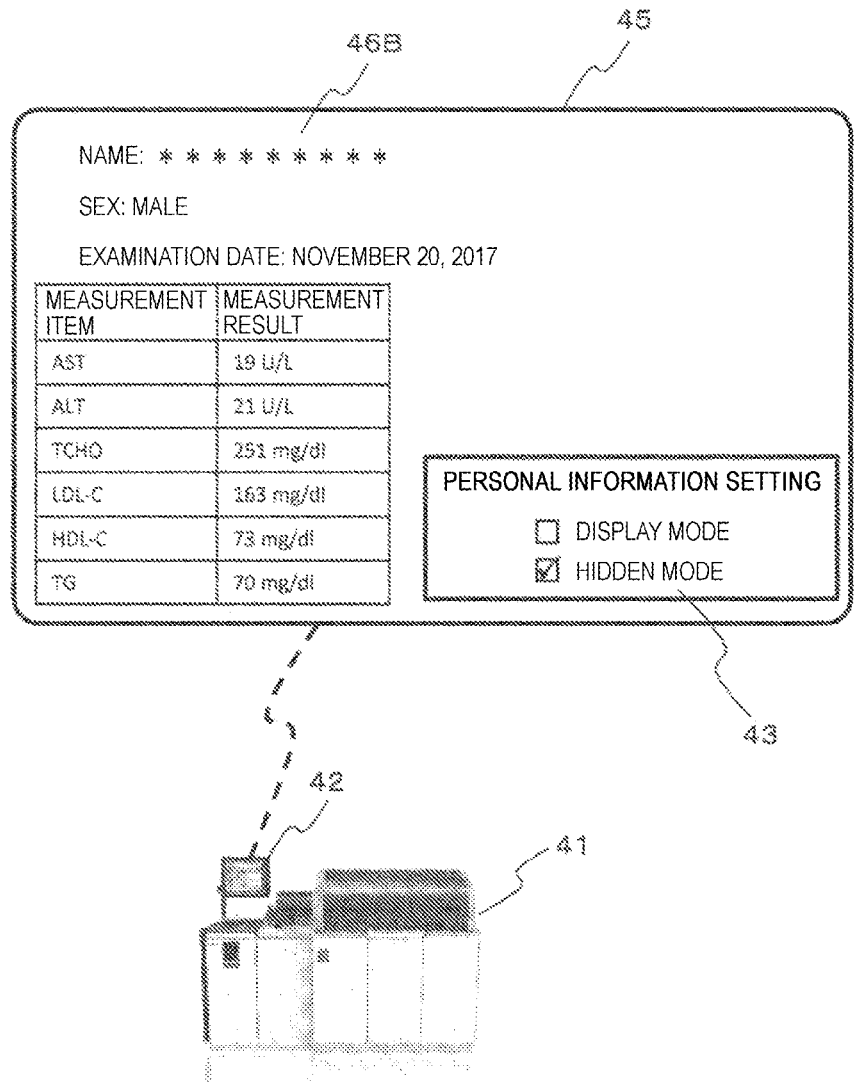
[FIG. 9]
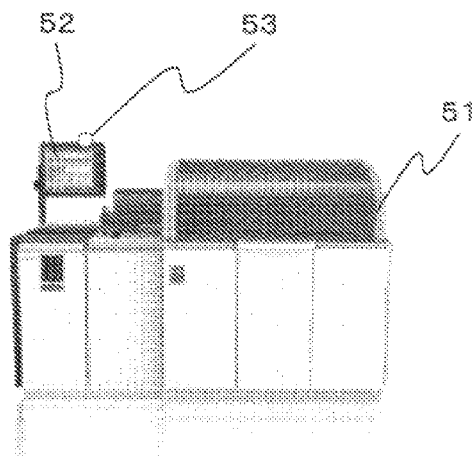

NAME: TARO YAMADA

SEX: MALE

EXAMINATION DATE: NOVEMBER 20, 2017

| MEASUREMENT ITEM | MEASUREMENT RESULT |
|---|---|
| AST | 19 U/L |
| ALT | 21 U/L |
| TCHO | 251 mg/dl |
| LDL-C | 163 mg/dl |
| HDL-C | 73 mg/dl |
| TG | 70 mg/dl |

NAME: * * * * * * * *

SEX: MALE

EXAMINATION DATE: NOVEMBER 20, 2017

| MEASUREMENT ITEM | MEASUREMENT RESULT |
|---|---|
| AST | 19 U/L |
| ALT | 21 U/L |
| TCHO | 251 mg/dl |
| LDL-C | 163 mg/dl |
| HDL-C | 73 mg/dl |
| TG | 70 mg/dl |

55

[FIG. 12]
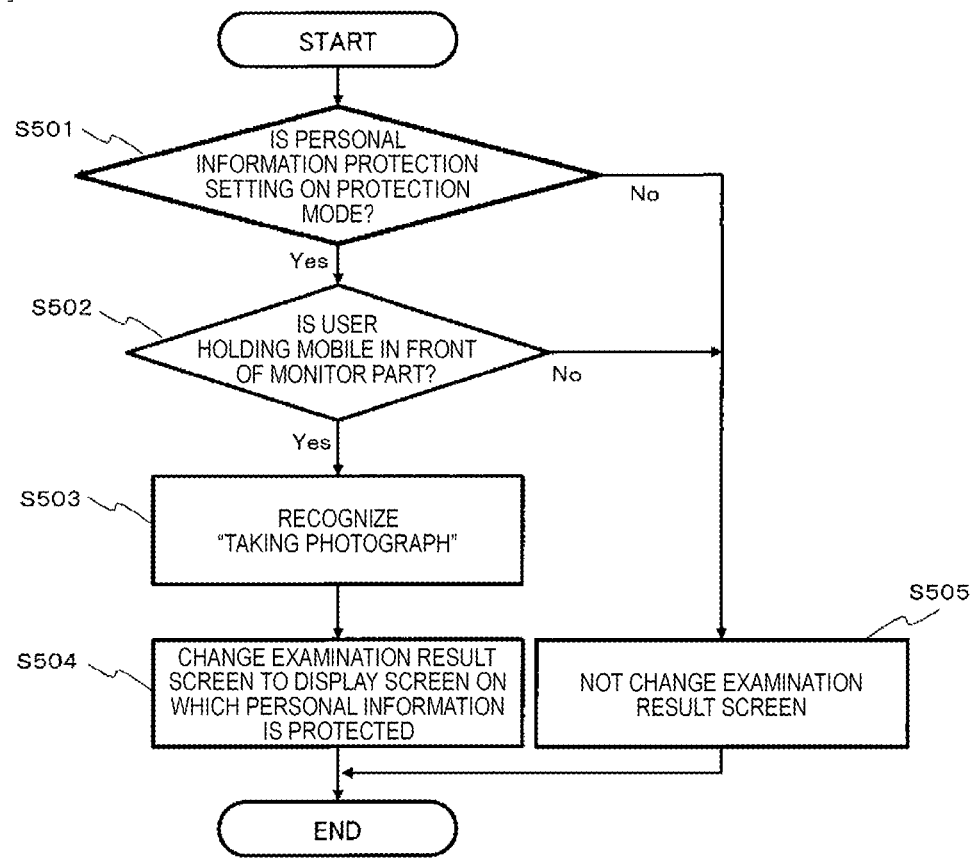

[FIG. 13]
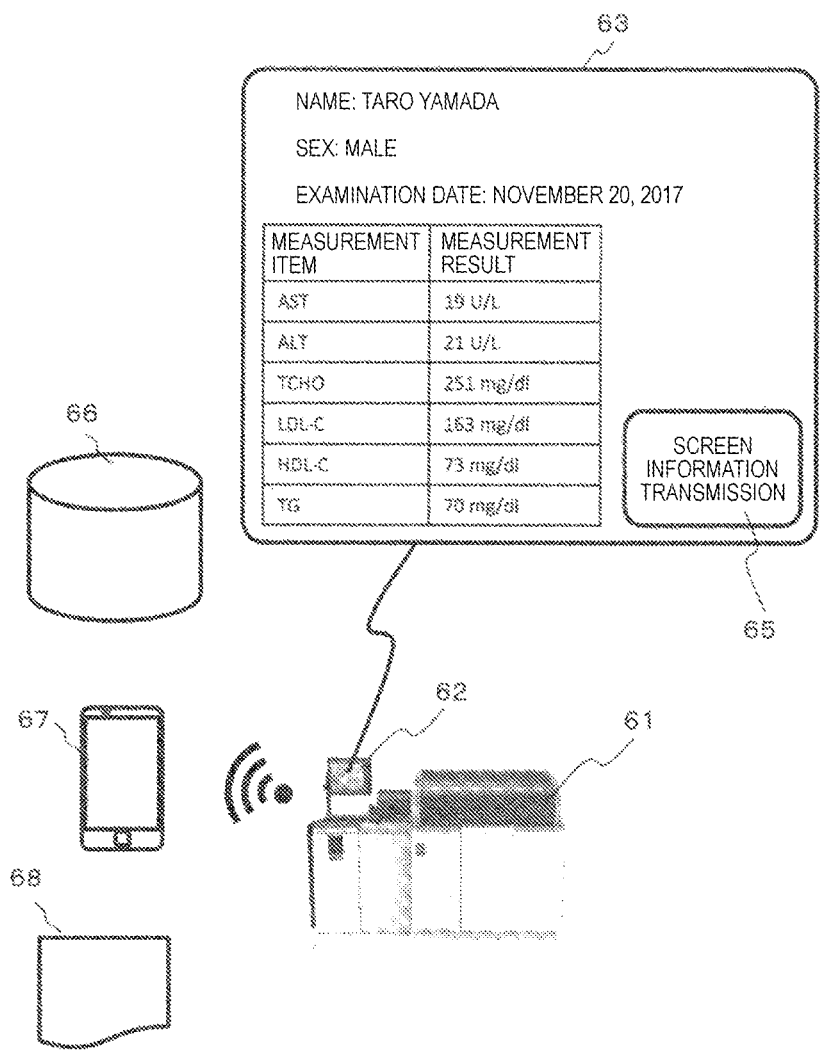

[FIG. 14]
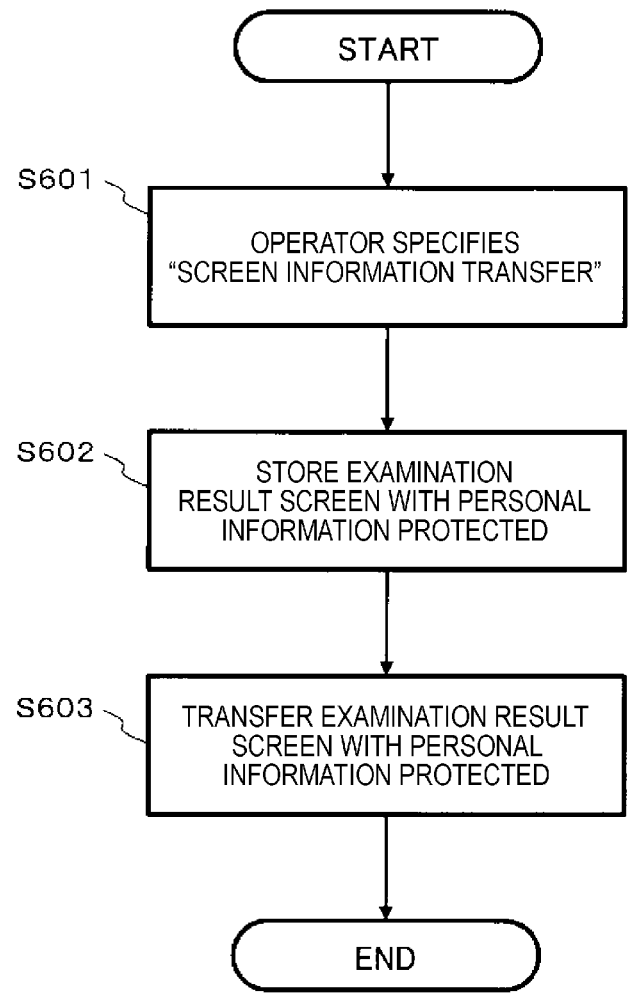

[FIG. 15]
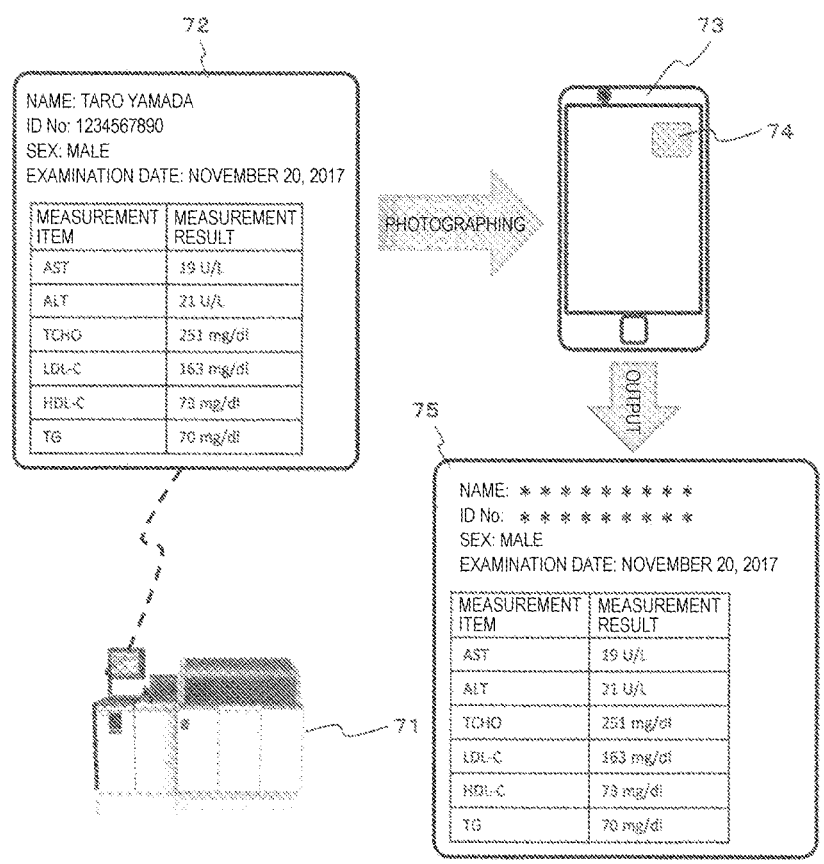

[FIG. 16]
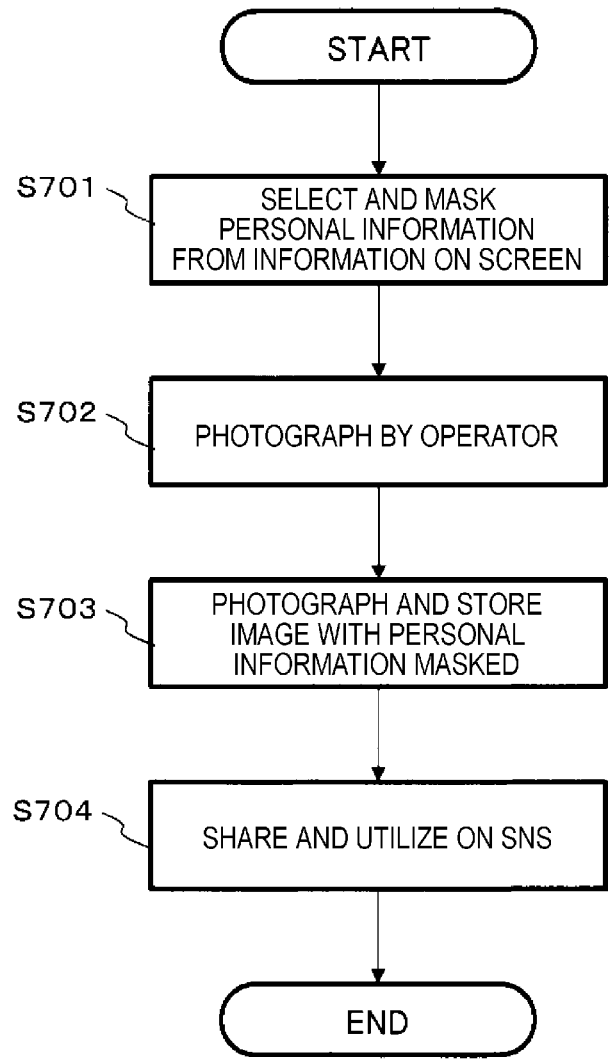

[FIG. 17]
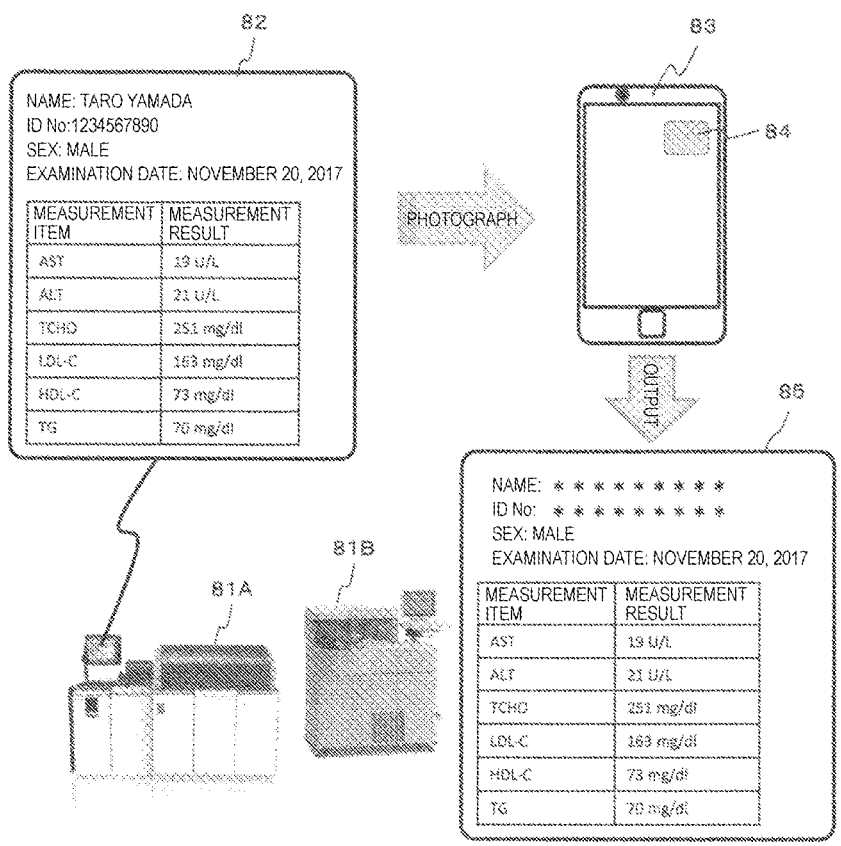

[FIG. 18]
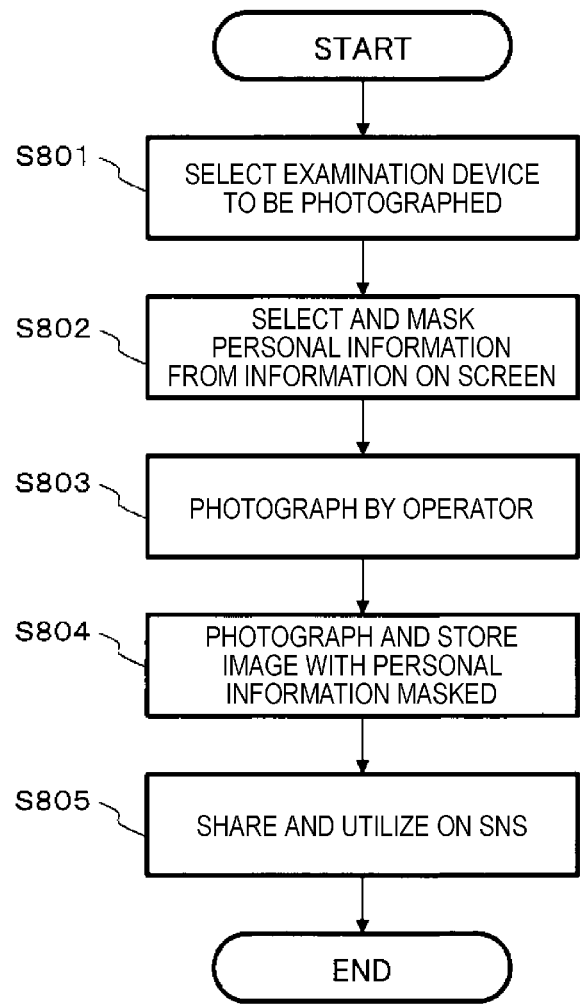

[FIG. 19]
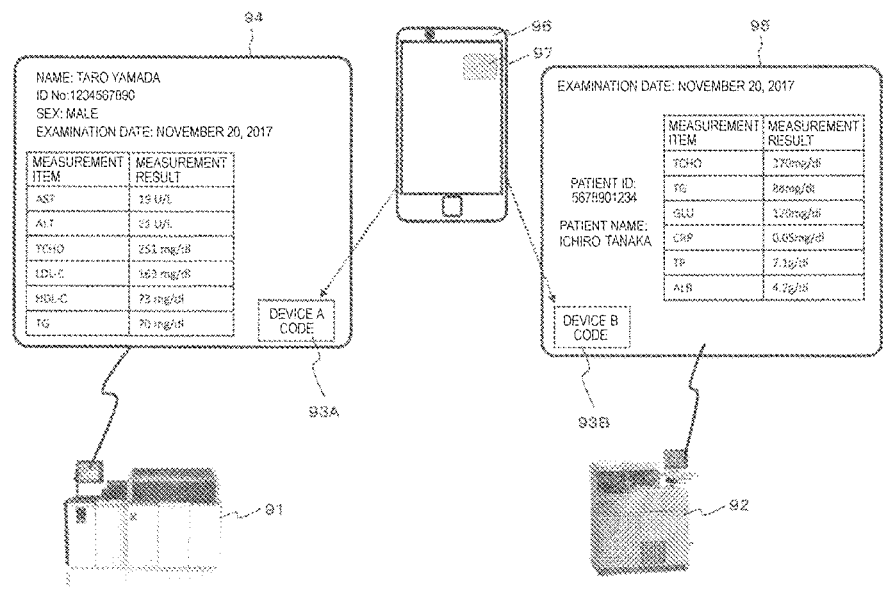

[FIG. 20]
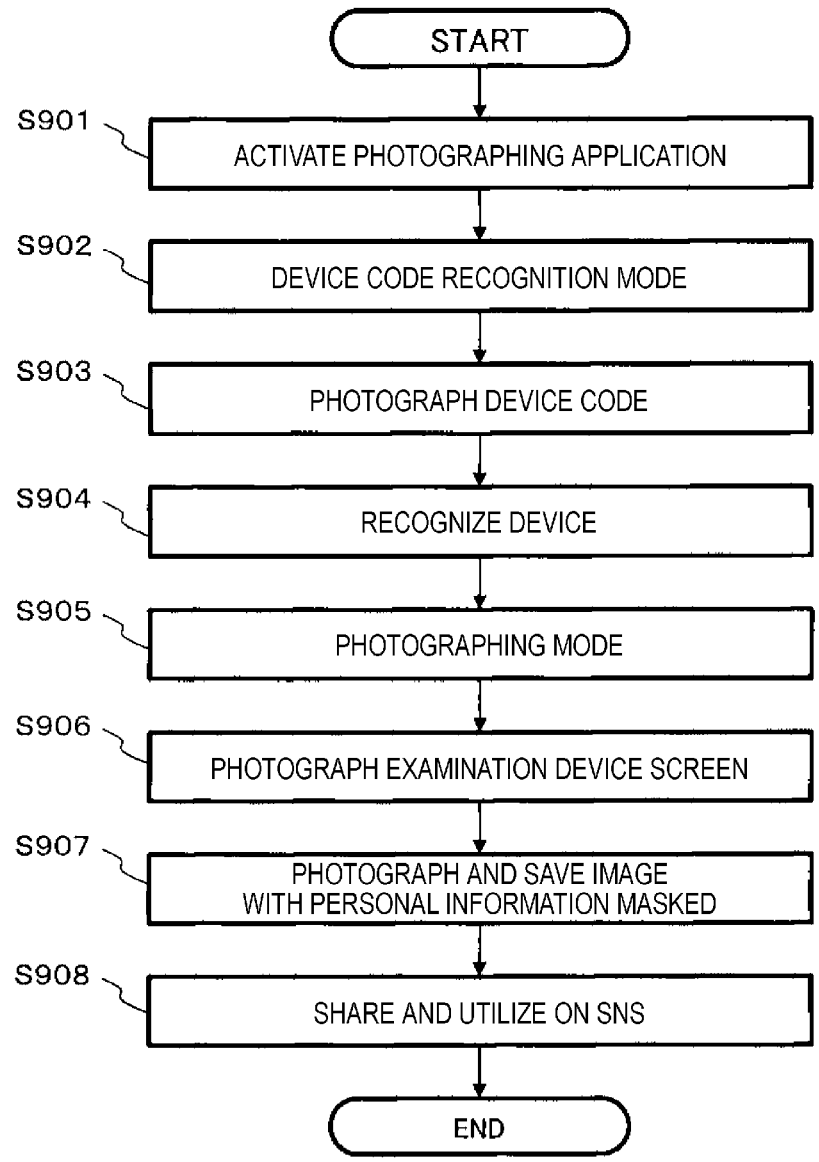

[FIG. 21]
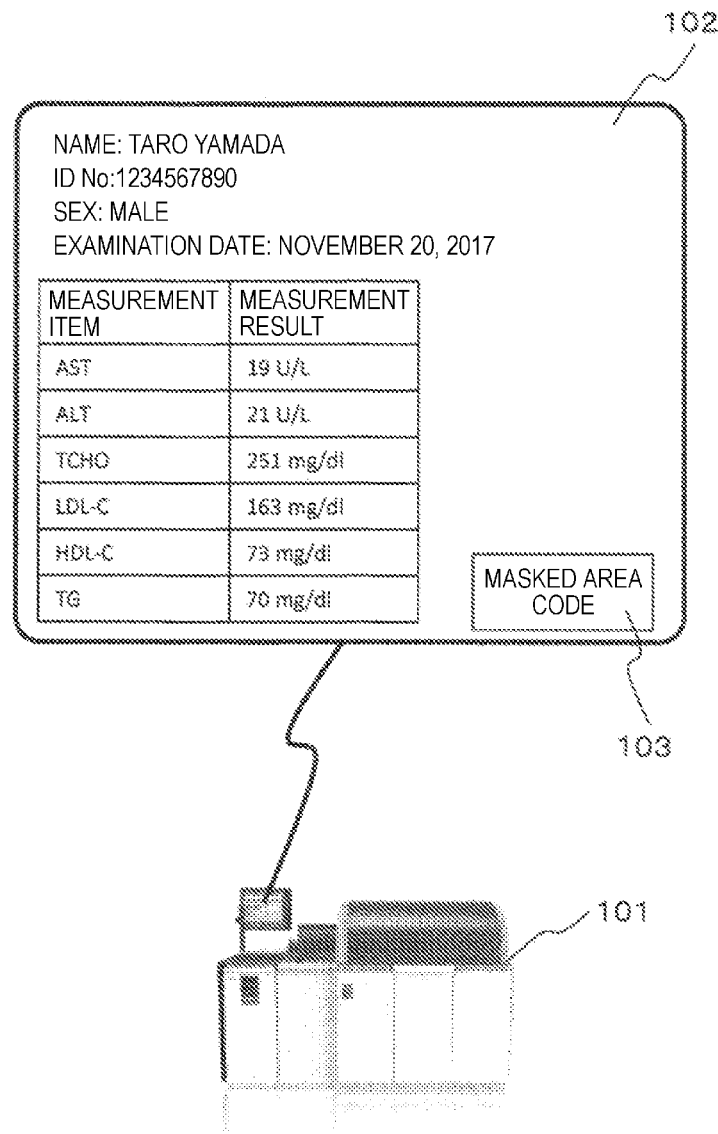

[FIG. 22]

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|
| 21 | 22 | 23 | 24 | 25 | 26 | 27 | 28 | 29 | 30 | 31 | 32 | 33 | 34 | 35 | 36 | 37 | 38 | 39 | 40 |
| 41 | 42 | 43 | 44 | 45 | 46 | 47 | 48 | 49 | 50 | 51 | 52 | 53 | 54 | 55 | 56 | 57 | 58 | 59 | 60 |
| 61 | 62 | 63 | 64 | 65 | 66 | 67 | 68 | 69 | 70 | 71 | 72 | 73 | 74 | 75 | 76 | 77 | 78 | 79 | 80 |
| 81 | 82 | 83 | 84 | 85 | 86 | 87 | 88 | 89 | 90 | 91 | 92 | 93 | 94 | 95 | 96 | 97 | 98 | 99 | 100 |
| 101 | 102 | 103 | 104 | 105 | 106 | 107 | 108 | 109 | 110 | 111 | 112 | 113 | 114 | 115 | 116 | 117 | 118 | 119 | 120 |
| 121 | 122 | 123 | 124 | 125 | 126 | 127 | 128 | 129 | 130 | 131 | 132 | 133 | 134 | 135 | 136 | 137 | 138 | 139 | 140 |
| 141 | 142 | 143 | 144 | 145 | 146 | 147 | 148 | 149 | 150 | 151 | 152 | 153 | 154 | 155 | 156 | 157 | 158 | 159 | 160 |
| 161 | 162 | 163 | 164 | 165 | 166 | 167 | 168 | 169 | 170 | 171 | 172 | 173 | 174 | 175 | 176 | 177 | 178 | 179 | 180 |
| 181 | 182 | 183 | 184 | 185 | 186 | 187 | 188 | 189 | 190 | 191 | 192 | 193 | 194 | 195 | 196 | 197 | 198 | 199 | 200 |
| 201 | 202 | 203 | 204 | 205 | 206 | 207 | 208 | 209 | 210 | 211 | 212 | 213 | 214 | 215 | 216 | 217 | 218 | 219 | 220 |
| 221 | 222 | 223 | 224 | 225 | 226 | 227 | 228 | 229 | 230 | 231 | 232 | 233 | 234 | 235 | 236 | 237 | 238 | 239 | 240 |
| 241 | 242 | 243 | 244 | 245 | 246 | 247 | 248 | 249 | 250 | 251 | 252 | 253 | 254 | 255 | 256 | 257 | 258 | 259 | 260 |

| 1 | 2 | | | | | | | | | 11 | 12 | 13 | 14 | 15 | 16 | 17 | 18 | 19 | 20 |
|---|---|---|---|---|---|---|---|---|---|---|---|---|---|---|---|---|---|---|---|
| 21 | 22 | | | | | | | | | 31 | 32 | 33 | 34 | 35 | 36 | 37 | 38 | 39 | 40 |
| 41 | 42 | 43 | 44 | 45 | 46 | 47 | 48 | 49 | 50 | 51 | 52 | 53 | 54 | 55 | 56 | 57 | 58 | 59 | 60 |
| 61 | 62 | 63 | 64 | 65 | 66 | 67 | 68 | 69 | 70 | 71 | 72 | 73 | 74 | 75 | 76 | 77 | 78 | 79 | 80 |
| 81 | 82 | 83 | 84 | 85 | 86 | 87 | 88 | 89 | 90 | 91 | 92 | 93 | 94 | 95 | 96 | 97 | 98 | 99 | 100 |
| 101 | 102 | 103 | 104 | 105 | 106 | 107 | 108 | 109 | 110 | 111 | 112 | 113 | 114 | 115 | 116 | 117 | 118 | 119 | 120 |
| 121 | 122 | 123 | 124 | 125 | 126 | 127 | 128 | 129 | 130 | 131 | 132 | 133 | 134 | 135 | 136 | 137 | 138 | 139 | 140 |
| 141 | 142 | 143 | 144 | 145 | 146 | 147 | 148 | 149 | 150 | 151 | 152 | 153 | 154 | 155 | 156 | 157 | 158 | 159 | 160 |
| 161 | 162 | 163 | 164 | 165 | 166 | 167 | 168 | 169 | 170 | 171 | 172 | 173 | 174 | 175 | 176 | 177 | 178 | 179 | 180 |
| 181 | 182 | 183 | 184 | 185 | 186 | 187 | 188 | 189 | 190 | 191 | 192 | 193 | 194 | 195 | 196 | 197 | 198 | 199 | 200 |
| 201 | 202 | 203 | 204 | 205 | 206 | 207 | 208 | 209 | 210 | 211 | 212 | 213 | 214 | 215 | 216 | 217 | 218 | 219 | 220 |
| 221 | 222 | 223 | 224 | 225 | 226 | 227 | 228 | 229 | 230 | 231 | 232 | 233 | 234 | 235 | 236 | 237 | 238 | 239 | 240 |
| 241 | 242 | 243 | 244 | 245 | 246 | 247 | 248 | 249 | 250 | 251 | 252 | 253 | 254 | 255 | 256 | 257 | 258 | 259 | 260 |

[FIG. 24]
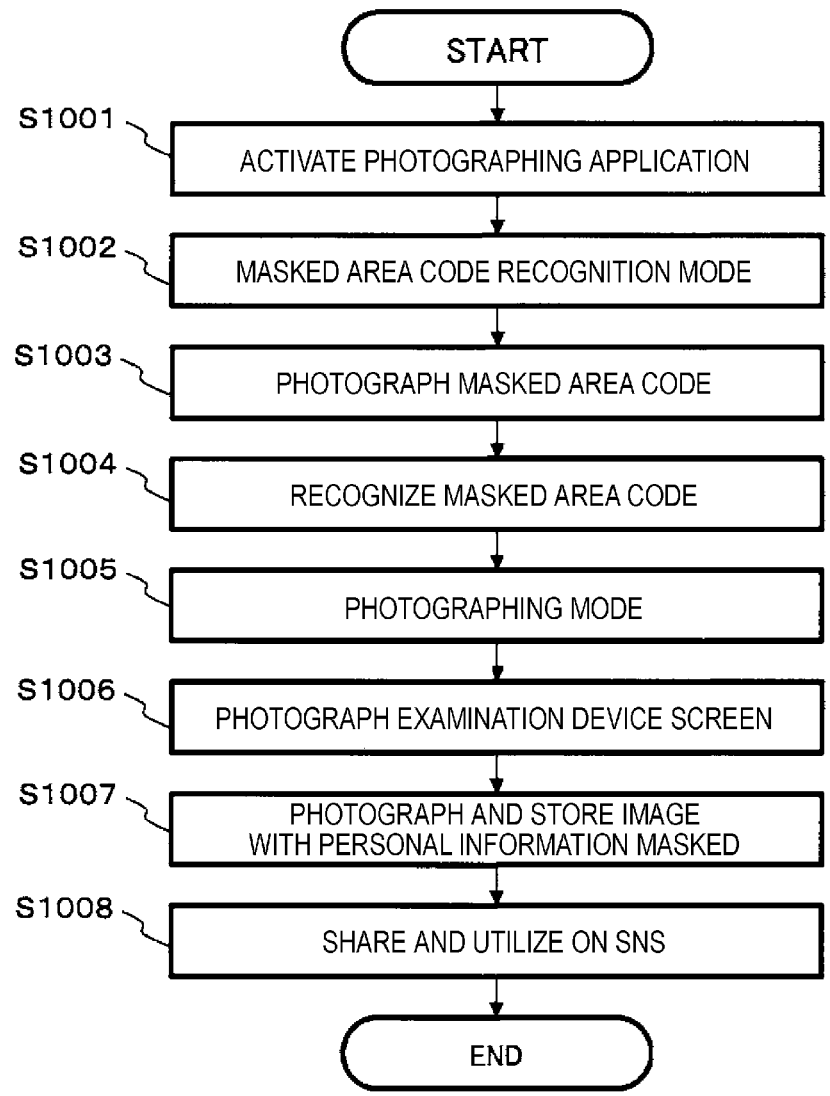

DISPLAY DEVICE, INFORMATION TERMINAL, PERSONAL INFORMATION PROTECTION METHOD, PROGRAM, AND RECORDING MEDIUM WHEREON PROGRAM IS RECORDED

TECHNICAL FIELD

The present invention relates to a display device, an information terminal, a personal information protection method, and a program and a recording medium for recording the program.

BACKGROUND ART

PTL 1 describes a device that switches the information to be displayed depending on the type of operator. PTL 1 describes that with the aim to reduce the risk of an engineer accidentally outputting personal information to the outside and for a user to output an analysis result including the required personal information, when the operator logs in to the specimen examination device, the information processing unit accepts the input of the user ID and password to authenticate the user, the patient attribute information such as the patient ID and the patient's name, the doctor in charge, ward, patient comment, and the like is output together with the examination result if the logged-in operator is a general user, while the examination result is output without outputting the patient attribute information if the logged-in operator is an engineer.

CITATION LIST

Patent Literature

PTL 1: JP-A-2011-033536

SUMMARY OF INVENTION

Technical Problem

The clinical examination device that analyzes clinical specimens records the analysis results obtained by examining the specimens collected from a subject and personal information that can identify a subject, such as a name, in association with each other. Such personal information that can identify a subject is required to be prevented from leaking to the outside in order to protect personal information.

The above-mentioned PTL 1 describes a technique to prevent personal information from being displayed in error without including at least a part of subject attribute information when operated by an operator belonging to the type of serviceman who performs maintenance.

Here, laboratory technicians who are users of the clinical examination device may discuss an operation method of the analysis device and a viewing method of patient data through group chat, which is a way of the information sharing network.

The group chat in the present invention is software or applications for various known social networking services (SNS) in which a plurality of people can connect at the same time and chat as a group among the chat functions and services that can communicate in real time, and examples thereof include LINE (registered trademark) and WeChat (registered trademark).

The use of such a group chat makes it possible to smoothly exchange information between laboratory technicians. For example, a laboratory technician who is not accustomed to operating an analysis device or an inexperienced laboratory technician can easily receive advice from an experienced laboratory technician, which contributes to the improvement of examination technology.

The information displayed on the analysis device that analyzes clinical specimens includes personal information that leads to the identification of the patient, but the display screen of the analysis device may be posted as it is on the group chat, and it is desired to apply a technique in which personal information is taken into consideration.

In the above PTL 1, it is not assumed that a user shares information on an examination result screen with an external user by using a CCD camera or a mobile, and a technique for further improving the protection of personal information is desired.

The present invention has been made in view of the above-mentioned problems and an object thereof is to provide a display device, an information terminal, a personal information protection method, and a program and a recording medium for recording the program, which suppress erroneous display of personal information to an external user as compared with the conventional case and sharing of examination result information is implemented smoothly.

Solution to Problem

The present invention includes a plurality of means for solving the above problems. One example thereof is a display device provided in at least one system among a clinical examination device, a laboratory information system, and a hospital information system including electronic medical records, which are operated by a medical practitioner, the display device including a display unit that displays an examination result screen that includes personal information for identifying a subject, and an arithmetic processing unit that identifies the personal information from the examination result screen being displayed on the display unit and executes an invalidation process for invalidating the identified personal information from the captured image including the examination result screen.

Further, another example is a personal information protection method in a system consisting of at least one among a clinical examination device, a laboratory information system, a hospital information system including electronic medical records, and an information terminal having a photographing function, which are operated by a medical practitioner, the method including a display process for displaying an examination result screen including personal information for identifying a subject on a display unit installed in the clinical examination device, the laboratory information system, or the hospital information system, an identification process for identifying the personal information from the examination result screen being displayed by the display process, and an invalidation process for invalidating the personal information identified in the identification process from the captured image including the examination result screen.

Advantageous Effects of Invention

According to the present invention, it is possible to suppress the erroneous display of personal information to an external user as compared with the conventional case, and sharing of examination result information can be implemented smoothly. Problems, configurations, and effects other than those mentioned above will be clarified by the description of the following embodiments.

BRIEF DESCRIPTION OF DRAWINGS

FIG. 1 is a diagram illustrating an example of a functional block diagram of a clinical examination device and a mobile according to a first embodiment of the present invention.

FIG. 2 is a diagram illustrating an example of a configuration and a display screen for protecting personal information in the clinical examination device and the mobile of the first embodiment of the present invention.

FIG. 3 is a diagram illustrating an example of the display screen of the mobile according to the first embodiment of the present invention.

FIG. 4 is a diagram showing an example of a setting screen for personal information protection in a clinical examination device, a terminal for a laboratory information system, and a terminal for a hospital information system according to a second embodiment of the present invention.

FIG. 5 is a diagram showing an example of a screen for selecting whether or not to display a personal information protection mark in the clinical examination device according to a third embodiment of the present invention.

FIG. 6 is a diagram showing an example of a screen for selecting whether or not to display a personal information protection mark in the clinical examination device according to the third embodiment of the present invention.

FIG. 7 is a diagram showing an example of a screen for switching personal information display in the clinical examination device according to a fourth embodiment of the present invention.

FIG. 8 is a diagram showing an example of a screen for switching personal information display in the clinical examination device according to the fourth embodiment of the present invention.

FIG. 9 is a diagram illustrating an outline of a configuration of a clinical examination device according to a fifth embodiment of the present invention.

FIG. 10 is a diagram showing an example of a screen for switching personal information display in the clinical examination device according to the fifth embodiment of the present invention.

FIG. 11 is a diagram showing an example of a screen for switching personal information display in the clinical examination device according to the fifth embodiment of the present invention.

FIG. 12 is a diagram illustrating an example of an operation flow in the clinical examination device according to the fifth embodiment of the present invention.

FIG. 13 is a diagram illustrating an outline of a configuration of a clinical examination device according to a sixth embodiment of the present invention.

FIG. 14 is a diagram illustrating an example of an operation flow in the clinical examination device according to the sixth embodiment of the present invention.

FIG. 15 is a diagram illustrating an example of a configuration and a display screen for protecting personal information in a mobile according to a seventh embodiment of the present invention.

FIG. 16 is a diagram illustrating an example of an operation flow in the mobile according to the seventh embodiment of the present invention.

FIG. 17 is a diagram illustrating an example of a configuration and a display screen for protecting personal information in a mobile according to an eighth embodiment of the present invention.

FIG. 18 is a diagram illustrating an example of an operation flow in a mobile according to the eighth embodiment of the present invention.

FIG. 19 is a diagram illustrating an example of a configuration and a display screen for protecting personal information in a clinical examination device and mobile of a ninth embodiment of the present invention.

FIG. 20 is a diagram illustrating an example of an operation flow in the clinical examination device and the mobile according to the ninth embodiment of the present invention.

FIG. 21 is a diagram illustrating an example of a configuration and a display screen for protecting personal information in a clinical examination device and mobile of a tenth embodiment of the present invention.

FIG. 22 is a diagram showing an example of the information held by a mask area code in the clinical examination device of the tenth embodiment of the present invention.

FIG. 23 is a diagram showing an example of the information held by the mask area code in the clinical examination device of the tenth embodiment of the present invention.

FIG. 24 is a diagram illustrating an example of an operation flow in the clinical examination device and the mobile according to the tenth embodiment of the present invention.

DESCRIPTION OF EMBODIMENTS

Hereinafter, embodiments of a display device, an information terminal, a personal information protection method, and a program and a recording medium for recording the program will be described with reference to the drawings.

First Embodiment

A first embodiment of a computer display device, an information terminal, a personal information protection method, and a program and a recording medium for recording the program will be described with reference to FIGS. 1 to 3.

First, a system to which the computer display device, the information terminal, the personal information protection method, and the program and the recording medium for recording the program are preferably applied, and a configuration for executing the system will be described with reference to FIG. 1. FIG. 1 is a functional block diagram of a clinical analysis device and a mobile that realize a computer display device, an information terminal, a personal information protection method, and a program and a recording medium for recording the program in this embodiment.

The computer program of this embodiment is intended to protect personal information by recognizing a personal information protection mark 10 (see FIG. 2) displayed on an examination result screen 3 (see FIG. 2) of a clinical examination device 1 with a camera 9b of a mobile 9 and processing designated personal information into a hidden image.

Therefore, the computer program of this embodiment to be executed by the system operated by a medical practitioner is executed by the clinical examination device 1 and the mobile 9 as shown in FIG. 1. In this embodiment, the medical practitioner who is the user is mainly a laboratory technician.

The clinical examination device 1 is a device that analyzes a specimen, such as blood or urine, collected from a patient and is, for example, an automatic biochemical analysis device or an automatic immunoassay device. As shown in FIG. 1, the clinical examination device 1 includes an analysis unit 1a, an analysis unit operation control unit 1b, an analysis arithmetic processing unit 1c, a recording unit 1d, a communication processing unit 1e, an arithmetic processing unit 1f, and a monitor part 2.

The analysis unit 1a is composed of known devices used for specimen analysis and the details thereof will be omitted.

The analysis unit operation control unit 1b is composed of a CPU, a memory, and the like that control the operation of each component in the clinical examination device 1 including the analysis unit 1a.

The analysis arithmetic processing unit 1c is composed of a CPU, a memory, and the like, and calculates the concentration of biological components contained in the specimen based on the analysis result of the specimen collected from a subject, which has been obtained by the analysis unit 1a.

The recording unit 1d is a recording medium such as a semiconductor memory such as a flash memory or a magnetic disk such as an HDD, in which recording data related to a specimen input into the clinical examination device 1 and analysis results are recorded. In the recording unit 1d, various computer programs and the like for controlling the operation of each device in the clinical examination device 1 and executing various arithmetic processes described later are recorded.

The recording unit 1d of this embodiment records, in particular, a computer program for executing a part of a display process for displaying the examination result screen 3 including personal information for identifying a subject as described later on the monitor part 2 and an identification process for identifying personal information from the examination result screen displayed on the monitor part 2 of the clinical examination device 1.

The communication processing unit 1e exchanges measurement item information and examination results by controlling the communication process with each mechanism in the clinical examination device 1 via a wireless or wired communication means, the communication process with the mobile 9, the laboratory information system (LIS), the hospital information system (HIS), an Internet server 100, and the like to link information, updates the content of information on the specimen recorded in the recording unit 1d and displays the content of the information on the specimen on the monitor part 2.

Note that LIS is a higher-level system of the clinical examination device 1 and controls the entire clinical examination device 1. Further, HIS is a system, such as an electronic medical record or an ordering system, for terminals operated by a doctor and is a system located above LIS.

The arithmetic processing unit 1f is composed of processing devices such as a CPU and a memory that execute a computer program recorded in the recording unit 1d and executes the display processing (display process) for causing the monitor part 2 to display the examination result screen 3 including personal information for identifying a subject. Further, as a part of the identification processing (identification process), the arithmetic processing unit 1f causes the monitor part 2 to display the specific personal information protection mark 10 on the examination result screen 3.

The case where the arithmetic processing unit 1f is composed of a device different from the analysis unit operation control unit 1b and the analysis arithmetic processing unit 1c described above is described, but two or more devices and systems may be integrated and shared and only the processes may be divided. Further, it is possible to assume that at least a part of the configurations is connected via a wired or wireless network. Further, the operation control process may be integrated into one program, may be divided into a plurality of programs, or may be a combination thereof. Further, a part or all of the programs may be realized by dedicated hardware or may be modularized.

The monitor part 2 is a display device that displays measurement item information and examination results. In particular, the monitor part 2 of this embodiment displays the examination result screen 3 including personal information that identifies a subject. The specific personal information protection mark 10 is displayed on the examination result screen 3.

Further, the mobile 9 is a smartphone or tablet terminal owned individually by a laboratory technician in general or attached to the clinical examination device 1, and includes a display unit 9a, a camera 9b, an arithmetic processing unit 9c, and a recording unit 9d, and a communication processing unit 9e.

The display unit 9a is a part that outputs information to be supplied to the laboratory technician who operates the mobile 9. For example, the display unit 9a is composed of a display or the like and displays the image captured by the camera 9b and information supplied from the arithmetic processing unit 9c.

The camera 9b is a portion that captures the examination result screen 3 and the like displayed on the monitor part 2 of the clinical examination device 1.

The arithmetic processing unit 9c is composed of processing devices such as a CPU, a memory, and the like for controlling the operation of each component in the mobile 9. The arithmetic processing unit 9c is composed of a CPU, a memory, and the like for executing a computer program recorded in the recording unit 9d and executes apart of the identification processing (identification process) for identifying personal information from the examination result screen 3 displayed on the monitor part 2 of the clinical examination device 1 or an invalidation processing (invalidation process) for invalidating the personal information identified in the identification processing from the captured image including the examination result screen 3.

Further, the arithmetic processing unit 9c executes a process of uploading only the captured image including the examination result screen 3 invalidated by the invalidation process in the group chat software or the group chat application.

In particular, the arithmetic processing unit 9c of the mobile 9 of the present embodiment identifies the area where the personal information is displayed by detecting the personal information protection mark 10 by image recognition as the above-mentioned identification processing and makes the identified area blanked or protected as the invalidation processing.

The recording unit 9d is composed of a semiconductor memory such as a flash memory in which various computer programs and the like for controlling the operation of each device in the mobile 9 and executing various arithmetic processes described later are recorded. In this embodiment, in particular, a computer program for executing a part of the above-mentioned identification processing, the invalidation processing, and processing or a process for uploading is recorded.

The communication processing unit 9e is a portion that transmits and receives information to and from the communication processing unit 1e of the clinical examination device 1 and the Internet server 100 using radio waves.

In this embodiment, the case where the system operated by the medical practitioner is the clinical examination device 1 and the mobile 9 having the imaging function is described, but the system is not limited thereto, and the computer program of the present invention can be applied to LIS and HIS in addition to the clinical examination device 1. In this case, it is necessary to install a monitor part for LIS or HIS. In the case of these LIS or HIS, the medical practitioner is mainly a laboratory technician or a doctor.

Further, the present embodiment describes the case where the recording medium that can be read by the processing device constituting the system operated by the medical practitioner is composed of the recording unit 1d provided in the clinical examination device 1 and the recording unit 9d provided in the mobile 9. However, the recording medium on which the computer program that causes the system to execute each of the above-mentioned processes and procedures is recorded is not limited thereto. For example, the recording medium can be at least one of the Internet server 100 as shown in FIG. 1, a semiconductor memory such as RAM, DRAM, or SRAM, a magnetic disk such as floppy disk, an optical disk such as MO, CD, DVD, Blu-ray (registered trademark), a semiconductor memory such as flash memory and may be appropriately distributed.

For example, the Internet server 100 can be installed in the system by the medical practitioner accessing the site and appropriately downloading it.

Further, although the case where the arithmetic processing unit if of the clinical examination device executes a part of the display processing and the identification processing and the arithmetic processing unit 9c of the mobile 9 executes a part of the identification processing and the invalidation processing has been described, the present invention is not limited to this configuration and the processing device that executes various processes and procedures as in each embodiment described later can be appropriately dispersed into at least one of the clinical examination device 1, LIS, HIS, and the mobile 9 having a photographing function.

Next, a method of protecting personal information achieved by preferably executing the program according to this embodiment will be described with reference to FIGS. 2 and 3. FIGS. 2 and 3 are configuration explanatory views of a personal information protection method in the clinical laboratory in this embodiment.

Roughly speaking, in the method of protecting personal information in this embodiment, the camera 9b of the mobile 9 recognizes the personal information protection mark 10 displayed on the examination result screen 3 of the clinical examination device 1, and by making the designated personal information a hidden image and uploading it, it is possible to smoothly realize a system that shares the examination result information while suppressing the leakage of personal information to the outside as compared with the conventional case.

First, the analysis unit 1a, the analysis unit operation control unit 1b, and the analysis arithmetic processing unit 1c of the clinical examination device 1 execute the analysis of the specimen collected from a subject and obtain the concentration of the predetermined component. The obtained measurement information is recorded in the recording unit 1d or the like of the clinical examination device 1 in a state associated with the information for identifying a subject.

Further, as shown in FIG. 2, the obtained measurement information is displayed on the monitor part 2 of the clinical examination device 1 as the examination result screen 3 including the measurement information (display process). On the examination result screen 3 including the measurement information, the name 4, the sex 5, and the examination date 6 are displayed as information indicating the attributes of the specimen. In addition, measurement items 7 and measurement results 8 of the specimen are also displayed.

In FIG. 2, "name" is displayed as "Taro Yamada" as a personal information item. Further, as shown in FIG. 2, the personal information protection mark 10 is displayed in an arrangement sandwiching the name 4 (a part of the identification process).

Regarding the examination result screen 3 including the measurement information, the user of the clinical examination device 1 may use the group chat application installed on the mobile 9 to consult with Advisor A or Advisor B of another medical institution.

At this time, in order to prevent the name 4 displayed on the examination result screen 3 from being transmitted to the external Advisor A and Advisor B, the following procedure is executed on the mobile 9.

As a premise, the mobile 9 is equipped with an application for photographing the examination result screen 3 of the clinical examination device 1. Further, the photographing application of the mobile 9 executes a process of recognizing the personal information protection mark 10 (a part of the identification process) and is added with a function of replacing the range sandwiched between the personal information protection marks 10 with the "*" mark (masking function) (invalidation process).

Such a photographing function or the like may be installed in the mobile 9 in advance and it is desirable that the medical practitioner installs the photographing function by an application download service on the Internet as appropriate.

When the examination result screen 3 is captured by the mobile 9 having such a photographing function, the area where the personal information is displayed is identified by detecting the personal information protection mark 10 by image recognition by the above-mentioned identification process. In addition, the area sandwiched between the personal information protection marks 10, on which the identified personal information is displayed, is hidden or masked (alternative display with a symbol mark).

As a result, as shown in FIG. 3, in the captured image 11 taken by the mobile 9, the information of the name 4 displayed on the examination result screen 3 including the measurement information is replaced with the "*" mark, and the screen after the replacement is stored in the recording unit 9d and displayed on the display unit 9a.

Although FIG. 3 describes the case where the symbol mark "*" is used as an alternative display, the alternative display is not limited to the symbol mark "*", and various marks can be used. Also, the alternative display is not limited to the case of being replaced with a symbol mark, it is possible to be replaced with character strings that do not make sense (characters that are extremely low to be used for personal names such as #, +, =, !, &, ?, %, @), and the area sandwiched by the personal information protection marks 10 can be displayed blank or can be displayed as a mosaic.

By providing the captured image 11 taken by the mobile 9 as shown in FIG. 3 obtained by the above-mentioned flow to the information sharing network for consultation with Advisor A and Advisor B of other medical institutions, both the personal information protection and information exchange with advisors of other medical institutions are realized.

Further, it is desirable that the mobile 9 has a function to allow to upload only the captured image 11 including the examination result screen 3 invalidated by the invalidation processing to the Internet server 100 when uploading the captured image to the information sharing network. This makes it possible to protect personal information more effectively.

This function to restrict the upload can be realized by various methods by installing the function in the group chat software or group chat application in advance, updating the function later by updating or modifying the program, or restricting the upload on the photographing application side.

Next, the effect of this embodiment will be described.

The above-described program and personal information protection method executed by the system operated by the medical practitioner according to the first embodiment of the present invention include the display processing for causing the monitor part 2 to display the examination result screen 3 including the personal information for identifying a subject, the identification processing for identifying personal information from the examination result screen 3 displayed in the display processing, and the invalidation processing for invalidating the personal information identified in the identification processing from the captured image including the examination result screen 3.

As a result, when discussions are held in the group chat about the operation method of the clinical examination device 1 and how to view the patient data, the captured image 11 which makes it impossible to identify the personal information is displayed on the group chat instead of the examination result screen 3 enabling to identify the personal information. Therefore, it is possible to smoothly exchange information and improve the examination technique without leaking personal information to the outside. That is, it is possible to suppress the erroneous display of personal information to an external user as compared with the conventional case, and sharing of examination result information is implemented smoothly.

Further, for the clinical examination device 1, LIS, or HIS, the specific personal information protection mark 10 is displayed on the examination result screen 3, and for the mobile 9, the personal information protection mark 10 is detected by image recognition to identify the area where personal information is displayed. Thus, in the invalidation processing, for the mobile 9, the area is blanked or protected, and thus, the personal information can be invalidated from the examination result screen 3 without any special procedure on the medical practitioner side and information can be exchanged in the same procedure as before. Therefore, it is expected that personal information can be protected without being shunned by the medical practitioner.

Further, in the group chat software or the group chat application, by further having a procedure of uploading only the captured image including the examination result screen 3 invalidated by the invalidation processing, the examination result screen 3 in which personal information is erroneously described can be more reliably suppressed from being displayed on the group chat.

Second Embodiment

A display device, an information terminal, a personal information protection method, and a program and a recording medium for recording the program according to a second embodiment of the present invention will be described with reference to FIG. 4. FIG. 4 is a diagram showing an example of a selection setting screen for personal information to be protected in this embodiment. In this embodiment, the same reference numerals are given to the same configurations as those in the first embodiment and the description thereof will be omitted. The same shall apply in the following embodiments.

As shown in FIG. 4, the present embodiment further includes a first selection process for displaying a personal information protection setting screen 18 for selecting the type of personal information to be identified on monitor parts 15a, 16a, and 17a.

The programs that execute the first selection process and the display process are recorded in the recording unit of a clinical examination device 15, the recording unit of a LIS terminal 16, and the recording unit of a HIS terminal 17, and are executed in each of them.

The program that executes the identification process or invalidation process is not particularly limited, and it is possible to be executed by recording a part of the program on the clinical examination device side and a part of the program on the mobile side, as long as the form of the first embodiment. Further, when the processing is completed on the clinical examination device side as in the third and fourth embodiments described later, it is possible to be recorded and executed on the clinical examination device side.

Further, regarding the first selection process, when most of the processes are completed on the mobile as in the case of the seventh and subsequent embodiments described later, it is possible to be recorded and executed on the mobile side.

The LIS terminal 16 and the HIS terminal 17 have a configuration equivalent to that of the clinical examination device 15 shown in FIG. 1, excluding the analysis unit 1a, the analysis unit operation control unit 1b, and the analysis arithmetic processing unit 1c. For example, the LIS terminal 16 is equipped with various hardware and software required for controlling the entire clinical examination device 15, and the HIS terminal 17 is equipped with various hardware and software required for an electronic medical record, an ordering system, or the like.

On the personal information protection setting screen 18, it is set whether or not to display regarding each personal information item. In FIG. 4, "name", "sex", "examination date", "ID No.", "medical record No.", "name of the doctor in charge", "ward and room", "measurement item name" and "measurement result" are described as examples of personal information items, and it is possible to validate or invalidate the protection by checking the check box in the case of protecting (invalidate) the information as personal information and unchecking the check box in the case of not protecting the information.

In the personal information set on the personal information protection setting screen 18, in the case of the first embodiment, the personal information protection mark 10 is displayed so as to surround the corresponding personal information.

The personal information protection setting screen 18 can be set unique to each of the clinical examination device 15, the LIS terminal 16, and the HIS terminal 17.

Also, the information to be protected can be added or deleted. For example, a field for selecting whether to protect additional information such as age can be added or deleted. The method for adding or deleting the information to be protected is not particularly limited. For example, it can be realized by the medical practitioner operating a terminal to manually add or delete information or selecting an item to be added or deleted by a pull-down method.

Other configurations and operations are substantially the same as the display device, the information terminal, the personal information protection method, the program, and the recording medium for recording the program of the first embodiment described above, and the details will be omitted.

The display device, the information terminal, the personal information protection method, the program, and the recording medium for recording the program according to the second embodiment of the present invention can also achieve almost the same effect as that of the display device, the information terminal, the personal information protection method, the program and the recording medium for recording the program of the first embodiment described above.

Further, by further having the first selection process of displaying the personal information protection setting screen 18 for selecting the type of personal information to be identified on the monitor parts 15a, 16a, and 17a, it is possible to appropriately select the personal information to be protected and more appropriate protection of personal information can be realized.

Third Embodiment

A display device, an information terminal, a personal information protection method, and a program and a recording medium for recording the program according to a third embodiment of the present invention will be described with reference to FIGS. 5 and 6. FIGS. 5 and 6 are diagrams showing an example of a screen for selecting whether or not to display the personal information protection mark in this embodiment.

For a user who does not photograph the examination result screen 3 of the clinical examination device 1 described in the first embodiment with the mobile 9 and a user who does not utilize the captured image on the SNS, "personal information protection mark 10" as shown in FIG. 2 may impair the visibility of necessary information.

Therefore, as shown in FIGS. 5 and 6, this embodiment further includes a second selection process to display a mode selection area 34 for selecting whether or not to display the personal information protection mark 10 to be displayed in the display process for the identification process on a monitor part 32 of a clinical examination device 31.

The program for executing this second selection process is recorded and executed on the clinical examination device 31, the LIS terminal 16, and the HIS terminal 17 as described in the second embodiment. The program for executing a part of the identification process or the invalidation process can be the same as in the second embodiment.

As shown in FIG. 5, the user selects the OFF mode in the mode selection area 34 in an examination result screen 31A. When it is recognized that the OFF mode has been selected, the arithmetic processing unit of the clinical examination device 31 causes the monitor part 32 to display the examination result screen 31A on which the personal information protection mark 10 is not displayed.

On the other hand, when the screen of the clinical examination device 31 is photographed by the mobile 9 and the captured image is utilized by the SNS, the user selects the ON mode in the mode selection area 34 as shown in FIG. 6. When it is recognized that the ON mode has been selected, the arithmetic processing unit of the clinical examination device 31 causes the monitor part 32 to display an examination result screen 31B on which the personal information protection mark 10 is displayed.

Other configurations and operations are substantially the same configurations and operations as the display device, the information terminal, the personal information protection method, and the program and the recording medium for recording the program of the above-mentioned first embodiment, and the details will be omitted.

The display device, the information terminal, the personal information protection method, and the program and the recording medium for recording the program according to the third embodiment of the present invention can also achieve almost the same effect as that of the display device, the information terminal, the personal information protection method, and the program and the recording medium for recording the program of the first embodiment described above.

Also, by further including the second selection process for displaying the mode selection area 34 for selecting whether or not to display the personal information protection mark 10 to be displayed on the monitor part 32, it is possible to correspond to various usage methods in the field.

Fourth Embodiment

A display device, an information terminal, a personal information protection method, and a program and a recording medium for recording the program according to a fourth embodiment of the present invention will be described with reference to FIGS. 7 and 8. FIGS. 7 and 8 are diagrams showing an example of a screen of a clinical examination device to which switching of personal information display is applied in this embodiment.

As shown in FIGS. 7 and 8, this embodiment further includes a third selection process for causing a monitor part 42 to display a personal information setting field for switching between a mode in which personal information is displayed and a mode in which personal information is hidden according to a user's instruction on examination result screens 44 and 45 of a clinical examination device 41.

In this embodiment, all the programs including the third selection process, the display process, the identification process, and the invalidation process are recorded and executed on the clinical examination device 41 side.

As shown in FIG. 7, the user has selected the "display mode" by selecting the personal information setting field 43 on the examination result screen 44 displayed on the monitor part 42 of the clinical examination device 41. According to the setting, the name 46A is displayed as "Taro Yamada" as personal information.

On the other hand, as shown in FIG. 8, on the examination result screen 45, the "hidden mode" is selected by selecting the personal information setting field 43. According to the setting, the symbol mark "*********" is displayed on the name 46B as personal information to prevent the identification of an individual.

Other configurations and operations are substantially the same configurations and operations as the display device, the information terminal, the personal information protection method, and the program and the recording medium for recording the program of the above-mentioned first embodiment, and the details will be omitted.

The display device, the information terminal, the personal information protection method, and the program and the recording medium for recording the program according to the fourth embodiment of the present invention can also achieve almost the same effect as that of the display device, the information terminal, the personal information protection method, and the program and the recording medium for recording the program of the first embodiment described above.

In addition, in the invalidation process, by further including the third selection process for causing the monitor part 42 to display the personal information setting field 43 for selecting a mode in which the personal information is invalidated by blanking or protecting the area where the personal information identified in the identification process is displayed and a mode in which the personal information is displayed as it is, it is possible to provide the examination result screen 45 in which personal information is invalidated to the information sharing network regardless of the configuration on the mobile side and personal information can be protected more effectively.

Fifth Embodiment

A display device, an information terminal, a personal information protection method, and a program and a recording medium for recording the program according to a fifth embodiment of the present invention will be described with reference to FIGS. 9 to 12. FIG. 9 is a diagram for illustrating the outline of the configuration of the clinical examination device, FIGS. 10 and 11 are diagrams showing an example of a screen for switching personal information display, and FIG. 12 is a diagram for illustrating an example of an operation flow.

In this embodiment, when whether or not to capture an examination result screen 54 displayed on a monitor part 52 with the mobile owned by the user is determined by image-processing the image captured by a camera 53 provided in a clinical examination device 51 and photographing is performed, an examination result screen 55 in which the area where the personal information is displayed is invalidated as in the above-mentioned third and fourth embodiments is automatically displayed.

In this embodiment, all the programs including the display process, the identification process, and the invalidation process are recorded and executed on the clinical examination device 51 side.

As shown in FIG. 9, the clinical examination device 51 is provided with a camera 53 for confirming whether or not the user has photographed the examination result screen 54 displayed on the monitor 52, in addition to the monitor part 52 for displaying the examination result screen 54 as shown in FIG. 10 and the examination result screen 55 as shown in FIG. 11.

Hereinafter, the operation of the clinical examination device 51 of this embodiment will be described with reference to FIG. 12. The clinical examination device 51 constantly executes the processing flow shown in FIG. 12 while the device power is ON or while the examination result screens 54 and 55 are displayed.

First, the arithmetic processing unit of the clinical examination device 51 determines whether or not the personal information protection setting mode required for the current clinical examination device 51 is the protection mode (step S501). For example, this is set by a method such as the third or fourth embodiments. When it is determined in this step that the protection mode is set, the process proceeds to step S502. On the other hand, when it is not determined that the protection mode is set, the process proceeds to step S505.

Next, the arithmetic processing unit processes the captured image on the camera 53 to determine whether or not the user is holding the mobile 9 in front of the monitor part 52 (step S502). When it is determined that the user is ready, the process proceeds to step S503. On the other hand, when it is not determined that the user is ready, the process proceeds to step S505.

Next, the arithmetic processing unit recognizes that the camera 53 built in the monitor part 52 "takes a photograph" (step S503).

Next, the arithmetic processing unit changes the screen displayed on the monitor part 52 to the examination result screen 55 in which personal information has been protected (step S504).

As shown in FIG. 11, on the examination result screen 55, the name 56B as a personal information item is displayed with a symbol mark of "*********".

On the other hand, when it is determined in step S501 that the mode is not the protection mode or when it is determined that the mobile 9 is not held, the screen displayed on the monitor part 52 is changed into the examination result screen 54 in which the personal information is not protected. (step S504).

As shown in FIG. 10, on the examination result screen 54, the name 56A as a personal information item is displayed as it is as "Taro Yamada".

Other configurations and operations are substantially the same configurations and operations as the display device, the information terminal, the personal information protection method, and the program and the recording medium for recording the program of the above-mentioned first embodiment, and the details will be omitted.

The display device, the information terminal, the personal information protection method, and the program and the recording medium for recording the program according to the fifth embodiment of the present invention can also achieve almost the same effect as that of the display device, the information terminal, the personal information protection method, and the program and the recording medium for recording the program of the first embodiment described above.

Further, in the invalidation process, even if the area where personal information is displayed in the examination result screen 54 displayed on the monitor part 52 is blanked or protected when the clinical examination device 51 detects photographing by the mobile, it is possible to provide the examination result screen 55 in which the personal information is invalidated to the information sharing network regardless of the configuration on the mobile side and the personal information can be protected more effectively.

In this embodiment, the case of detecting whether or not the examination result screens 54 and 55 are photographed by the camera 53 has been described, but the method of detecting whether or not the examination result screens 54 and 55 are photographed is not limited thereto, and for example, it is possible to detect by a notification from the mobile side that the mobile camera application has been activated. This notification may be replaced with detection by the camera 53, or both may be executed in no particular order.

Sixth Embodiment

A display device, an information terminal, a personal information protection method, and a program and a recording medium for recording the program according to a sixth embodiment of the present invention will be described with reference to FIGS. 13 and 14. FIG. 13 is a diagram for illustrating the outline of the configuration of the clinical examination device and FIG. 14 is a diagram for illustrating an example of the operation flow.

In this embodiment, as shown in FIG. 13, an image in which the personal information is automatically erased by taking a screenshot of the examination result screen 63 according to the instruction selected by a screen information transfer 65 on a monitor part 62 of a clinical examination device 61 and the image is transferred to a mobile 67 for personal use or attached to the device, uploaded to an SNS server 66, or output to a printer 68.

The timing of invalidating the personal information is not particularly limited and the personal information can be invalidated when, for example, the screen information transfer 65 is selected. However, it is sufficient if the personal information in the screenshot image can be invalidated at any time before uploading after the screenshot.

In this embodiment, all the programs including the display process, the identification process, the invalidation process, and the upload process are recorded and executed on the clinical examination device 61 side.

Hereinafter, the operation of the clinical examination device 61 of this embodiment will be described with reference to FIG. 14.

First, the arithmetic processing unit of the clinical examination device 61 recognizes that "the screen information transfer 65" has been identified by the user (step S601).

Next, the arithmetic processing unit of the clinical examination device 61 saves a screenshot image masked or hidden by preset personal information (step S602). The screenshot image to be saved is, for example, as shown in FIG. 11 above.

Next, the arithmetic processing unit of the clinical examination device 61 outputs a screenshot image in which personal information has been protected according to a user's instruction to an output means such as the SNS server 66, the mobile 67, or the printer 68 designated by the user (step S603).

Other configurations and operations are substantially the same configurations and operations as the display device, the information terminal, the personal information protection method, and the program and the recording medium for recording the program of the above-mentioned first embodiment, and the details will be omitted.

The display device, the information terminal, the personal information protection method, and the program and the recording medium for recording the program according to the sixth embodiment of the present invention can also achieve almost the same effect as that of the display device, the information terminal, the personal information protection method, and the program and the recording medium for recording the program of the first embodiment described above.

Further, in the invalidation process, even if the clinical examination device 61 outputs the screen information in which the area where personal information is displayed from the examination result screen 63 is blanked or protected, regardless of the configuration on the mobile side, it is possible to provide the examination result screen with the personal information invalidated to the information sharing network.

Seventh Embodiment

A display device, an information terminal, a personal information protection method, and a program and a recording medium for recording the program according to a seventh embodiment of the present invention will be described with reference to FIGS. 15 and 16. FIG. 15 is a diagram for illustrating an example of a configuration and a display screen for protecting personal information in a mobile and FIG. 16 is a diagram for illustrating an example of an operation flow.

In this embodiment, a dedicated photographing application 74 is prepared in a mobile 73 for each clinical examination device 71, and the arithmetic processing unit of the mobile 73 identifies an area in the examination result screen 72 where personal information is displayed.

In this embodiment, the program including the display process is recorded on the clinical examination device 71 side and the program including the identification process and the invalidation process is recorded on the mobile 73 side, and the programs are executed.

As shown in FIG. 15, the mobile 73 is equipped with the photographing application 74 having a dedicated personal information protection photographing function corresponding to the clinical examination device 71. When the examination result screen 72 is photographed by the photographing application 74, an image in which personal information has been masked, such as an examination result image 75, is acquired.

The examination result screen 72 displayed on the clinical examination device 71 is basically a screen peculiar to the model number of the device and the device manufacturer and the area where personal information is displayed can be identified to some extent from the peculiar examination result screen. Therefore, the area to be invalidated can also be identified. Therefore, a dedicated photographing application is prepared in advance for each clinical examination device, LIS, and HIS, and the area where personal information has been described is identified and invalidated.

Hereinafter, the operation of the mobile 73 of this embodiment will be described with reference to FIG. 16.

First, the user (user) of the mobile 73 activates the photographing application 74 corresponding to the clinical examination device 71 mounted on the mobile 73. Next, on the screen of the activated application, the personal information to be protected is selected. FIG. 15 shows a case where "name" and "ID No." are selected.

Next, as shown in FIG. 16, the arithmetic processing unit of the mobile 73 selects personal information from the information on the examination result screen 72 displayed on the clinical examination device 71 and performs the masking process (step S701).

After that, when it is recognized that the user has performed the operation to photograph the examination result screen 72 (step S702), the arithmetic processing unit of the mobile 73 stores the examination result image 75 protected by masking the personal information ("name" and "ID No.") in a recording unit or the like (step S703).

After that, the examination result image 75 is uploaded on the Internet server 100 (step S704) and the user can share the uploaded examination result image 75 on the SNS and consult the contents.

Other configurations and operations are substantially the same configurations and operations as the display device, the information terminal, the personal information protection method, and the program and the recording medium for recording the program of the above-mentioned first embodiment, and the details will be omitted.

The display device, the information terminal, the personal information protection method, and the program and the recording medium for recording the program according to the seventh embodiment of the present invention can also achieve almost the same effect as that of the display device, the information terminal, the personal information protection method, and the program and the recording medium for recording the program of the first embodiment described above.

In addition, for each clinical examination device 71, LIS, or HIS, the mobile 73 identifies the area where personal information is displayed from the examination result screen 72 by image processing, and thus, regardless of the configuration on the clinical examination device 71 side, it is possible to provide the examination result image 75 with the personal information invalidated to the information sharing network and the existing clinical examination device 71, LIS, and HIS can also achieve both appropriate personal information protection and sharing of the examination result information.

Eighth Embodiment

A display device, an information terminal, a personal information protection method, and a program and a recording medium for recording the program according to an eighth embodiment of the present invention will be described with reference to FIGS. 17 and 18. FIG. 17 is a diagram illustrating an example of a configuration and a display screen for protecting personal information in a mobile and FIG. 18 is a diagram illustrating an example of an operation flow.

In this embodiment, the types of clinical examination devices 81A and 81B are selected in a photographing application 84 of a mobile 83, and an area where personal information is displayed by image processing from an examination result screen 82 is identified according to the selection result of the device.

In this embodiment, the program including the display process is recorded on the clinical examination devices 81A and 81B, and the program including the identification process and the invalidation process is recorded on the mobile 83 side, and the programs are executed.

As shown in FIG. 17, the types of the clinical examination devices 81A and 81B are recorded in the mobile 83 and the photographing application 84 having a personal information protection photographing function according to the type of the selected clinical examination devices 81A and 81B is installed.

As described in the seventh embodiment, basically, the area where the personal information to be invalidated is described can be identified from the examination result screen displayed on the clinical examination device, LIS, and HIS by finding out the device. Therefore, by selecting the types of the clinical examination devices 81A and 81B in the photographing application 84 of the mobile 83, the area where the personal information is described is identified from the examination result screen 82 and an invalidated examination result image 85 is generated.

Hereinafter, the operation of the mobile 83 of this embodiment will be described with reference to FIG. 18.

First, when the user selects which of the clinical examination devices 81A and 81B to be photographed by the photographing application 84 in the mobile 83, the arithmetic processing unit of the mobile 83 identifies the type thereof (step S801). Here, a case where the clinical examination device 81A is selected will be described as an example.

Next, the arithmetic processing unit of the mobile 83 selects personal information from the information on the examination result screen 82 displayed on the clinical examination device 81A and performs masking processing (step S802).

After that, when it is recognized that the user has performed the operation to photograph the examination result screen 82 (step S803), the arithmetic processing unit of the mobile 83 stores the examination result image 85 protected by masking the personal information (step S804).

After that, the examination result image 85 is uploaded on the Internet server 100 (step S805) and the user can share the uploaded examination result image 85 on the SNS and consult the contents.

When photographing an image of the clinical examination device 81B, the user only needs to select the clinical examination device 81B in the device selection step S801.

Other configurations and operations are substantially the same configurations and operations as the display device, the information terminal, the personal information protection method, and the program and recording medium for recording the program of the above-mentioned first embodiment, and the details will be omitted.

The display device, the information terminal, the personal information protection method, and the program and recording medium for recording the program according to the eighth embodiment of the present invention can also achieve almost the same effect as that of the display device, the information terminal, the personal information protection method, and the program and recording medium for recording the program of the first embodiment described above.

Further, by selecting the types of the clinical examination devices 81A and 81B and identifying the area where the personal information is displayed by image processing from the examination result screen 82 according to the selection, regardless of the configuration on the side of the clinical examination devices 81A and 81B, it is possible to provide the examination result image 85 in which the personal information is invalidated to the information sharing network. Further, there is an advantage that it is not necessary to prepare a dedicated photographing application for each device as in the seventh embodiment.

Ninth Embodiment

A display device, an information terminal, a personal information protection method, and a program and a recording medium for recording the program according to a ninth embodiment of the present invention will be described with reference to FIGS. 19 and 20. FIG. 19 is a diagram illustrating an example of a configuration and a display screen for protecting personal information in a clinical examination device and a mobile, and FIG. 20 is a diagram illustrating an example of an operation flow.

As described in the seventh and eighth embodiments, the area where the personal information to be invalidated has been described can be identified from the examination result screen displayed on the clinical examination device, LIS, and HIS by finding out the device.

Therefore, in this embodiment, as shown in FIG. 19, the types of clinical examination devices 91 and 92 are recognized by a photographing application 97 of a mobile 96 recognizing device codes 93A and 93B for identifying the types of the devices in examination result screens 94 and 95 displayed on the monitor part to identify the area where the personal information is described and an invalidated examination result screen is generated.

In this embodiment, the program including the display process is recorded on the clinical examination devices 91 and 92 side, and the program including the identification process and the invalidation process is recorded on the mobile 96 side, and the programs are executed.

The device codes 93A and 93B in this embodiment are, for example, dedicated codes for identifying the device type displayed on the examination result screens 94 and 95 of the clinical examination devices 91 and 92, but in addition to this, the device code can be various information that can identify the device, such as the name and model number of the device displayed on the examination result screens 94 and 95, the name and version of the information processing software, and the like.

Hereinafter, the operation of the mobile 96 of this embodiment will be described with reference to FIG. 20.

First, when it is recognized that the user activates the photographing application 97 of the mobile 96 (step S901), the arithmetic processing unit of the mobile 96 proceeds to the device code recognition mode (step S902).

Next, when it is recognized that the user has photographed the device codes 93A and 93B (step S903), the arithmetic processing unit of the mobile 96 recognizes the types of the clinical examination devices 91 and 92 by image processing (step S904).

For example, when photographing the examination result screen 94 of the clinical examination device 91, the device code 93A is read. When the device code 93A is read by the mobile 96, the mobile 96 recognizes that the object to be photographed is the clinical examination device 91.

Next, the arithmetic processing unit of the mobile 96 proceeds to the photographing mode (step S905).

After that, when it is recognized that the user recognizes the operation to photograph the examination result screens 94 and 95 has performed (step S906), the arithmetic processing unit of the mobile 96 stores the examination result image in which personal information has been protected by masking (step S907).

After that, the examination result image is uploaded on the Internet server 100 (step S908) and the user can share the uploaded examination result image on the SNS and consult the contents.

When photographing an image of the clinical examination device 92, the user may read the device code 93B displayed on the examination result screen 95 of the clinical examination device 92 in step S904.

After starting the photographing application 97 in step S901, steps S902 to S904 are omitted and it is possible to directly proceed to the photographing mode of step S905 to recognize the device codes 93A and 93B from the captured examination result screens 94 and 95 and to identify the area where the personal information is displayed from the device codes 93A and 93B to invalidate the area. In this process, the process for recognizing the device codes 93A and 93B becomes unnecessary and the convenience is further improved.

Other configurations and operations are substantially the same configurations and operations as the display device, the information terminal, the personal information protection method, and the program and recording medium for recording the program of the above-mentioned first embodiment, and the details will be omitted.

The display device, the information terminal, the personal information protection method, and the program and recording medium for recording the program according to the ninth embodiment of the present invention can also achieve almost the same effect as that of the display device, the information terminal, the personal information protection method, and the program and recording medium for recording the program of the first embodiment described above.

Further, the mobile 96 identifies the area where the personal information is displayed by identifying the code for recognizing the device or system included in the examination result screens 94 and 95, which also makes it possible to provide the examination result screen in which personal information has been invalidated by processing mainly on the mobile 96 side to the information sharing network. Further, it is not necessary to prepare a dedicated application for each device as in the seventh embodiment and it is not necessary for the user to select the device as in the eighth embodiment, which has the advantage of being more user-friendly.

Tenth Embodiment

A display device, an information terminal, a personal information protection method, and a program and a recording medium for recording the program according to a tenth embodiment of the present invention will be described with reference to FIGS. 21 to 24. FIG. 21 is a diagram illustrating an example of a configuration and a display screen for protecting personal information in a clinical examination device and a mobile. FIGS. 22 and 23 are diagrams showing examples of the information held by the mask area code. FIG. 24 is a diagram illustrating an example of an operation flow.

In this embodiment, in the display process, a clinical examination device 101 and the like cause the examination result screen 102 to display any one of a code for identifying the area to be invalidated in the invalidation process, a code for identifying the area not to be invalidated, and a code for identifying the area to be invalidated and the area not to be invalidated. In addition, the mobile reads the code displayed in the display process to identify the area where personal information is displayed.

As shown in FIG. 21, a mask area code 103 is displayed on the examination result screen 102 displayed on the monitor part of the clinical examination device 101. In addition, the mobile is equipped with an application that reads the information of the mask area code 103 and takes a photograph based on the read information.

The mask area code 103 is a code that identifies which area is displayed or which area is not displayed when the screen is photographed by a mobile or a portable terminal.

As shown in FIGS. 22 and 23, the mask area code 103 is a code that subdivides the examination result screen displayed on the monitor part of the clinical examination device 101 into 260 areas, numbers the subdivided areas, and identifies which area 106 is to be masked.

FIG. 22 shows an initial state, that is, a state without a mask area. FIG. 23 shows a code that identifies that the range divided into areas 3 to 10 and 23 to 30 is masked.

The mask area code is not limited to the code that describes the information for identifying the area where personal information is displayed but can be either a code that describes the information for identifying the area where personal information is not displayed, or a code that describes the information for identifying the area where personal information is displayed and the area where information is not displayed.

In this embodiment, the program including the display process is recorded on the clinical examination device 101 side, and the program including the identification process and the invalidation process is recorded on the mobile side.

Hereinafter, the operation of the clinical examination device 101 and the mobile of this embodiment will be described with reference to FIG. 24.

First, when it is recognized that the user has activated the photographing application of the mobile (step S1001), the mobile arithmetic processing unit proceeds to the mask area code recognition mode (step S1002).

Next, when it is recognized that the user has photographed the mask area code 103 (step S1003), the mobile arithmetic processing unit recognizes the mask area code (step S1004).

Next, the arithmetic processing unit of the mobile 96 proceeds to the photographing mode (step S1005).

After that, when it is recognized that the user has performed the operation to photograph the examination result screen 102 (step S1006), the arithmetic processing unit of the mobile stores the examination result image in which the personal information has been protected by masking the personal information based on the mask area code 103 (step S1007).

After that, the examination result image is uploaded on the Internet server 100 (step S1008) and the user can share the uploaded examination result image on the SNS and consult the contents.

Other configurations and operations are substantially the same configurations and operations as the display device, the information terminal, the personal information protection method, and the program and recording medium for recording the program of the above-mentioned first embodiment, and the details will be omitted.

The display device, the information terminal, the personal information protection method, and the program and recording medium for recording the program according to the tenth embodiment of the present invention can also achieve almost the same effect as that of the display device the information terminal, the personal information protection method, and the program and recording medium for recording the program of the first embodiment described above.

Further, in the display process, the clinical examination device 101 causes the examination result screen 102 to display any one of the mask area code 103 for identifying the area to be invalidated in the invalidation process, the code for identifying the area not to be invalidated, and the code for identifying the area to be invalidated and the area not to be invalidated, and the mobile read the code to identify the area where personal information is displayed, which makes it possible to invalidate the personal information from the examination result screen 102 without taking special procedures on the medical practitioner side and information can be exchanged in the same procedure as before.

<Others>

The present invention is not limited to the above embodiments and includes various modifications. The above-mentioned embodiments have been described in detail in order to explain the present invention in an easy-to-understand manner and are not necessarily limited to those having all the described configurations.

It is also possible to replace a part of the configuration of one embodiment with the configuration of another embodiment, and it is also possible to add the configuration of another embodiment to the configuration of one embodiment. It is also possible to add, delete, and replace a part of the configuration of each embodiment with another configuration.

REFERENCE SIGNS LIST 1, 15, 31, 41, 51, 61, 71, 81A, 81B, 91, 92, 101 . . . clinical examination device 1a . . . analysis unit
1b . . . analysis unit operation control unit
1c . . . analysis arithmetic processing unit
1d . . . recording unit
1e . . . communication processing unit
1f . . . arithmetic processing unit
2, 15a, 16a, 17a, 32, 42, 52, 62 . . . monitor part (display unit)
3, 31A, 31B, 44, 45, 54, 55, 63, 72, 82, 94, 95, 102 . . . examination result screen (clinical examination screen)
9, 67, 73, 83, 96 . . . mobile (information terminal)
9a . . . display unit
9b, 53 . . . camera
9c . . . arithmetic processing unit
9d . . . recording unit
9e . . . communication processing unit
10 . . . personal information protection mark (symbol mark)
11 . . . captured image
16 . . . LIS terminal
17 . . . HIS terminal
18 . . . personal information protection setting screen
34 . . . mode selection area
43 . . . personal information setting field
65 . . . screen information transfer
66 . . . SNS server
68 . . . printer
74, 84, 97 . . . photographing application
75, 85 . . . examination result image
93A, 93B . . . device code
100 . . . Internet server
103 . . . mask area code
106 . . . area

The invention claimed is:

1. A display device provided in at least one system among a clinical examination device, a laboratory information system, and a hospital information system including electronic medical records, which are operated by a medical practitioner, the display device comprising:
a display unit that displays an examination result screen that includes personal information for identifying a subject; and
an arithmetic processing unit that identifies the personal information from the examination result screen being displayed on the display unit and executes an invalidation process, based on a mask area code, for invalidating the identified personal information from the captured image including the examination result screen, wherein
the mask area code is a code that subdivides the examination result screen and identifies which area is displayed or not displayed.

2. The display device according to claim 1, wherein the arithmetic processing unit executes a first selection process for displaying on the display unit a selection screen for selecting the type of the personal information to be identified.

3. The display device according to claim 1, wherein the arithmetic processing unit executes a mode in which a symbol mark for identifying the personal information is displayed on the examination result screen and a mode in which the symbol mark is not displayed.

4. The display device according to claim 1, wherein the arithmetic processing unit executes a third selection process for displaying on the display a selection unit for selecting a mode in which the personal information is invalidated by blanking or protecting the area where the identified personal information is displayed, and a mode in which the personal information is displayed as it is.

5. The display device according to claim 1, wherein
in the invalidation process, when the arithmetic processing unit detects photographing by the information terminal, the arithmetic processing unit blanks or protects the area where the personal information is displayed in the examination result screen displayed on the display unit.

6. The display device according to claim 1, wherein
in the invalidation process, the arithmetic processing unit outputs screen information in which the area where the personal information is displayed is blanked or protected from the examination result screen.

7. An information terminal having a photographing function used by a medical practitioner who operates a system consisting of at least one among a clinical examination device, a laboratory information system, and a hospital information system including electronic medical records, the information terminal wherein
the area where the personal information is displayed is identified by detecting a mask area code that identifies the personal information from an examination result screen including the personal information that identifies a subject displayed on the display unit of the system by image recognition, and the identified area is invalidated by being blanked or protected, wherein
the mask area code is a code that subdivides the examination result screen and identifies which area is displayed or not displayed.

8. An information terminal having a photographing function used by a medical practitioner who operates a system consisting of at least one among a clinical examination device, a laboratory information system, and a hospital information system including electronic medical records, the information terminal wherein
for each of the clinical examination device, the laboratory information system, or the hospital information system, the area where the personal information is displayed is identified by image processing from an examination result screen including the personal information that identifies a subject displayed on the display unit of the system, and the identified area is invalidated, based on a mask area code, by being blanked or protected, wherein
the mask area code is a code that subdivides the examination result screen and identifies which area is displayed or not displayed.

9. The information terminal according to claim 8, wherein
the type of the clinical examination device, the laboratory information system, or the hospital information system is selected and according to the selection, the area where the personal information is displayed by image processing from the examination result screen is identified.

10. The information terminal according to claim 8, wherein
the mask area code is a code for recognizing a device or a system included in the examination result screen, and
the area where the personal information is displayed is identified based on the recognized mask area code.

11. The information terminal according to claim 8, wherein
the area where personal information is displayed is identified by reading any one among a mask area code for identifying the area to be invalidated, a mask area code for identifying the area not to be invalidated, and a mask area code for identifying the area to be invalidated and the area not to be invalidated, which have been displayed on the examination result screen.

12. The information terminal according to claim 7, wherein
only the captured image including the invalidated examination result screen is uploaded in group chat software or a group chat application.

13. A personal information protection method in a system consisting of at least one among a clinical examination device, a laboratory information system, a hospital information system including electronic medical records, and an information terminal having a photographing function, which are operated by a medical practitioner, the method comprising:
a display process for displaying an examination result screen including personal information for identifying a subject on a display unit installed in the clinical examination device, the laboratory information system, or the hospital information system;
an identification process for identifying the personal information from the examination result screen being displayed by the display process; and
an invalidation process for invalidating the personal information identified in the identification process from the captured image including the examination result screen, based on a mask area code, wherein
the mask area code is a code that subdivides the examination result screen and identifies which area is displayed or not displayed.

14. The personal information protection method according to claim 13, wherein
in the identification process, a specific symbol mark is displayed on the examination result screen for the clinical examination device, the laboratory information system, or the hospital information system, and the area where the personal information is displayed is identified by detecting the symbol mark by image recognition for the information terminal, and
in the invalidation process, the area is blanked or protected for the information terminal.

15. The personal information protection method according to claim 13, further comprising:
a first selection process of displaying on the display unit a selection screen for selecting the type of personal information to be identified in the identification process.

16. The personal information protection method according to claim 14, further comprising:
a second selection process of displaying on the display unit a selection unit for selecting whether or not to display the symbol mark to be displayed in the identification process.

17. The personal information protection method according to claim 13, further comprising:
a third selection process of displaying on the display unit a selection unit for selecting a mode in which the personal information is invalidated in the invalidation process by blanking or protecting the area where the personal information identified in the identification process is displayed, and a mode in which the personal information is displayed as it is.

18. The personal information protection method according to claim 13, wherein
in the invalidation process, the area where the personal information is displayed in the examination result screen displayed on the display unit is blanked or protected when the clinical examination device, the laboratory information system, or the hospital information system is detected to be photographed by the information terminal.

19. The personal information protection method according to claim 13, wherein
in the invalidation process, screen information in which the area where the personal information is displayed is blanked or protected from the examination result screen is output to the clinical examination device, the laboratory information system, or the hospital information system.

20. The personal information protection method according to claim 13, wherein
for each of the clinical examination device, the laboratory information system, or the hospital information system, in the identification process, the area where the personal information is displayed is identified from the examination result screen by image processing with respect to the information terminal.

21. The personal information protection method according to claim 20, wherein
the type of the clinical examination device, the laboratory information system, or the hospital information system is selected, and according to the selection, the area where the personal information is displayed is identified from the examination result screen by image processing with respect to the information terminal in the identification process.

22. The personal information protection method according to claim 13, wherein
in the identification process, for the information terminal, the mask area code is a code for recognizing a device or a system included in the examination result screen, and
the area where the personal information is displayed is identified based on the recognized mask area code.

23. The personal information protection method according to claim 13, wherein
in the display process, for the clinical examination device, the laboratory information system, or the hospital information system, any one among a mask area code for identifying the area to be invalidated in the invalidation process, a mask area code for identifying the area not to be invalidated, and a mask area code for identifying the area to be invalidated and the area not to be invalidated is displayed on the examination result screen, and
in the identification process, for the information terminal, the code is read to identify the area where personal information is displayed.

24. The personal information protection method according to claim 13, further comprising:
a process of uploading only the captured image including the examination result screen invalidated by the invalidation process in group chat software or a group chat application.

25. A non-transitory computer readable storage medium storing a program that is executable by at least one among a clinical examination device, a laboratory information system, a hospital information system including electronic medical records, and an information terminal having a photographing function, which are operated by a medical practitioner, the program comprising:
a display procedure for displaying on the display device an examination result screen including personal information for identifying a subject,
an identification procedure for identifying the personal information from the examination result screen being displayed by the display procedure, and
an invalidation procedure, based on a mask area code, for invalidating the personal information identified in the identification procedure from the captured image including the examination result screen, wherein
the display device is installed in the clinical examination device, the laboratory information system, or the hospital information system, and
the mask area code is a code that subdivides the examination result screen and identifies which area is displayed or not displayed.

26. A recording medium readable by a processing device constituting a system operated by a medical practitioner, wherein
the recording medium records a computer program, and
when the computer program is executed by the processing device, the system is caused to execute each procedure according to claim 25.

* * * * *